(12) United States Patent
Moss

(10) Patent No.: US 8,409,169 B1
(45) Date of Patent: Apr. 2, 2013

(54) CATHETER AND METHOD OF MAKING THE SAME

(76) Inventor: Gerald Moss, White Plains, NY (US)

( * ) Notice: Subject to any disclaimer, the term of this patent is extended or adjusted under 35 U.S.C. 154(b) by 431 days.

(21) Appl. No.: 12/819,118

(22) Filed: Jun. 18, 2010

Related U.S. Application Data

(60) Provisional application No. 61/218,355, filed on Jun. 18, 2009.

(51) Int. Cl.
*A61M 25/00* (2006.01)

(52) U.S. Cl. .................................... 604/526; 604/524

(58) Field of Classification Search .............. 604/170.02, 604/164.13, 524, 526, 536
See application file for complete search history.

(56) References Cited

U.S. PATENT DOCUMENTS

| 4,899,787 | A | * | 2/1990 | Ouchi et al. | 138/131 |
| 2008/0097331 | A1 | * | 4/2008 | Spivey et al. | 604/164.13 |

* cited by examiner

*Primary Examiner* — Kevin C Sirmons
*Assistant Examiner* — Deanna K Hall
(74) *Attorney, Agent, or Firm* — Schmeiser, Olsen & Watts LLP

(57) ABSTRACT

A method of manufacturing a catheter includes positioning a resilient tube in a vacuum tube. An outer periphery of the resilient tube is sealed to the vacuum tube so a vacuum region can be formed therebetween. A dimension of a channel of the resilient tube is adjustable in response to adjusting the pressure of the atmosphere of the vacuum region. The dimension of the channel is adjusted so that a reinforcement member can be positioned therein.

5 Claims, 24 Drawing Sheets

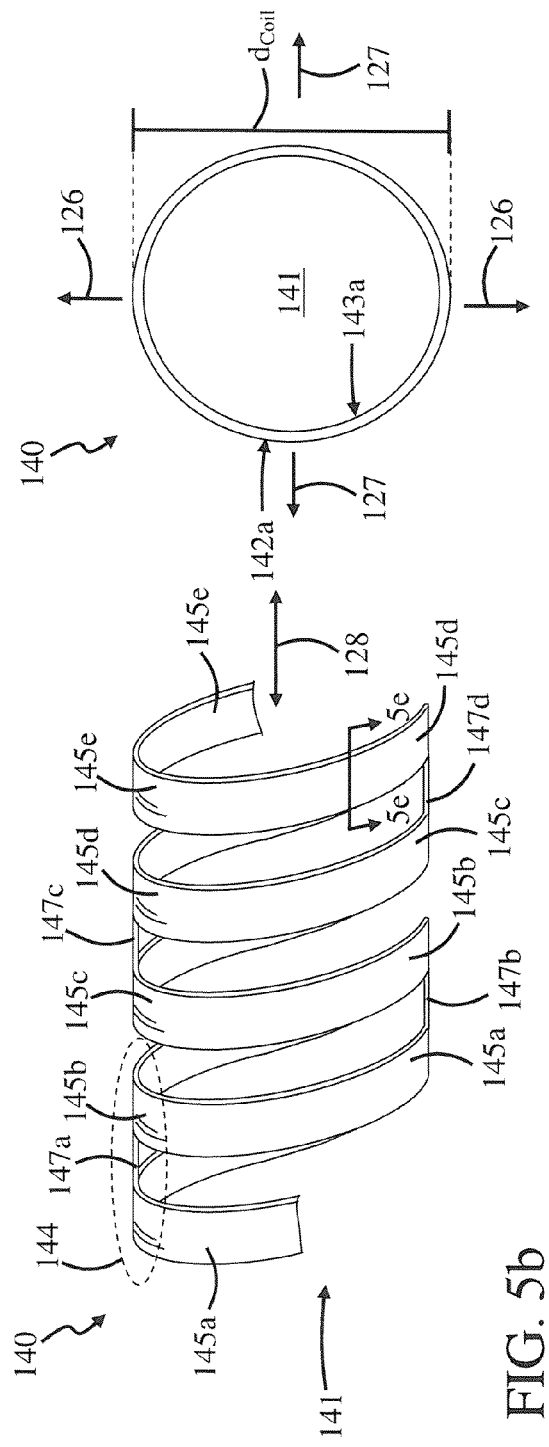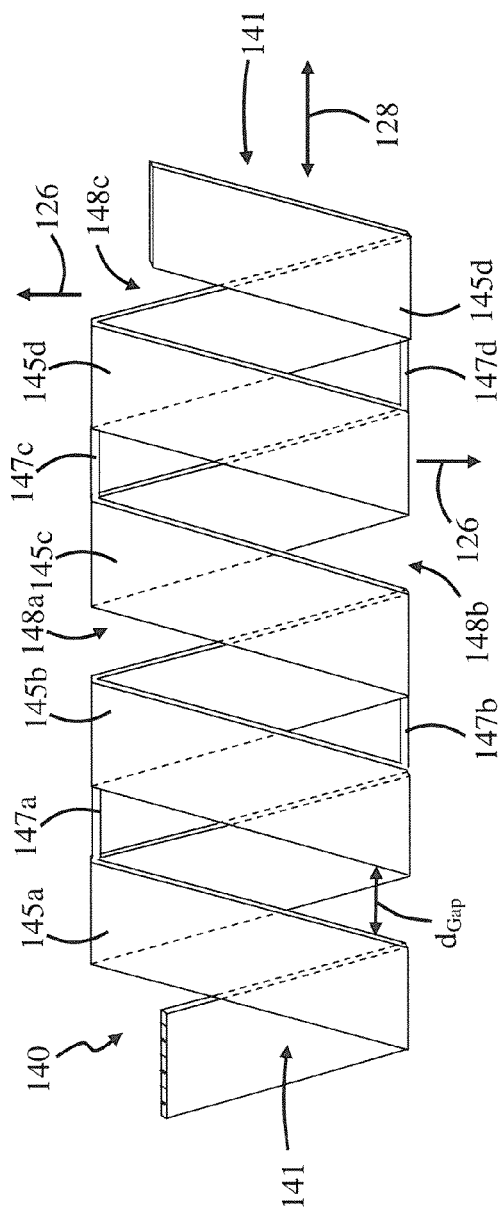

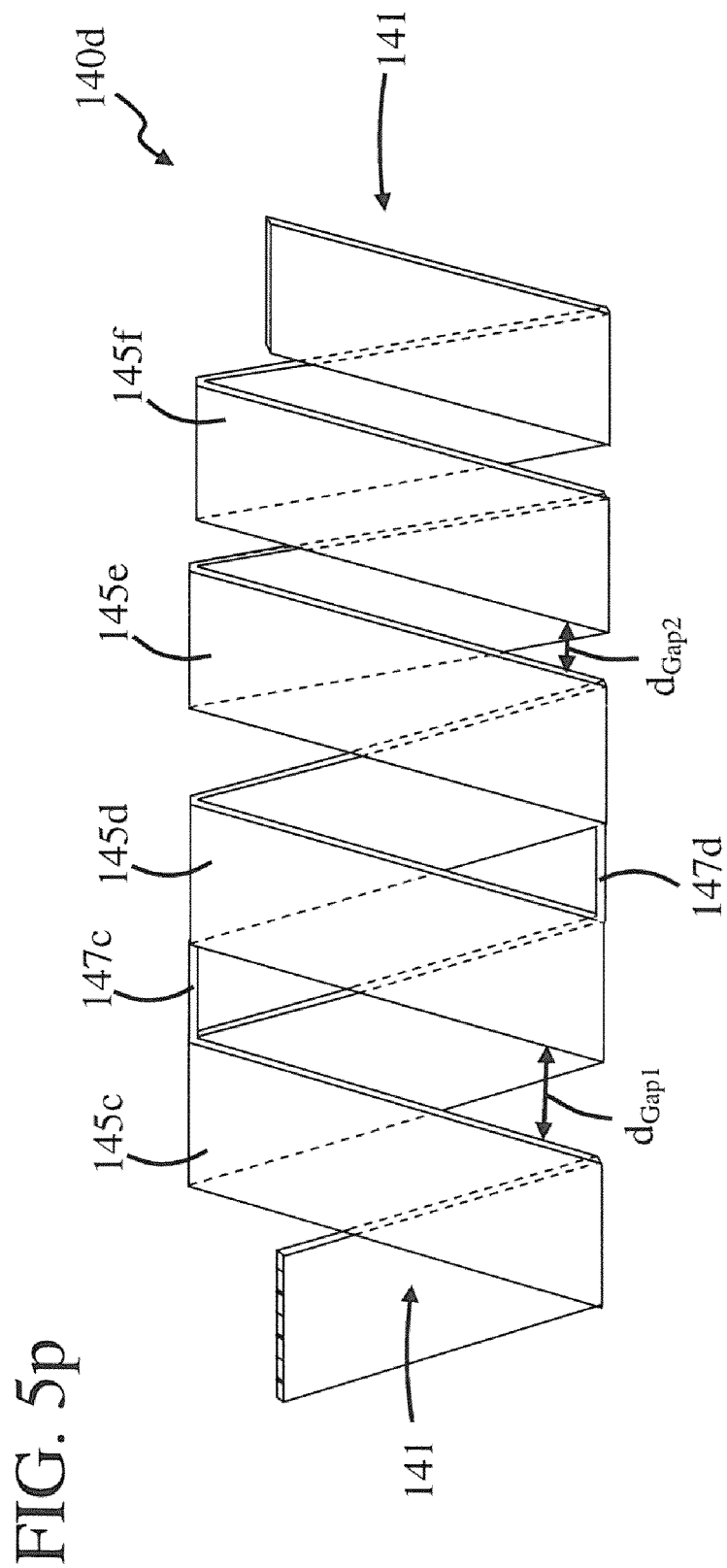

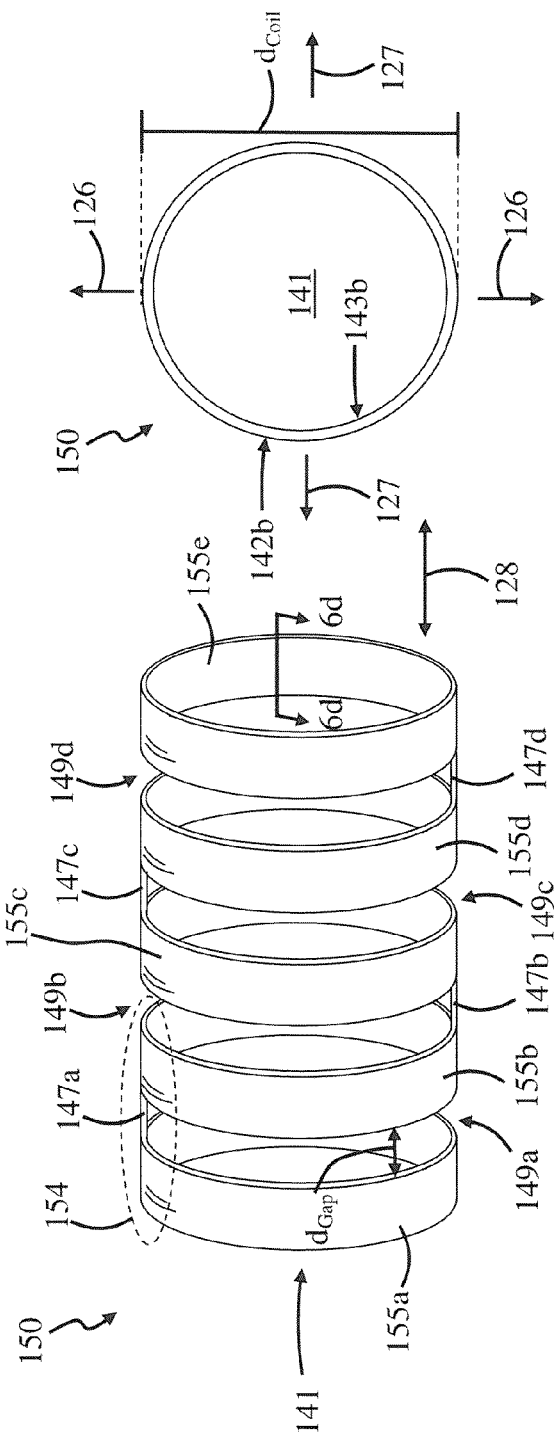
FIG. 6a
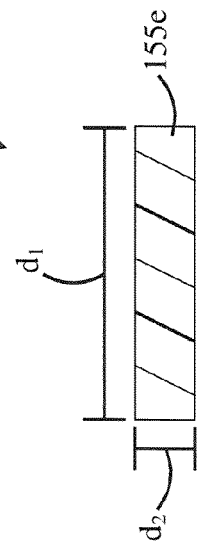
FIG. 6b
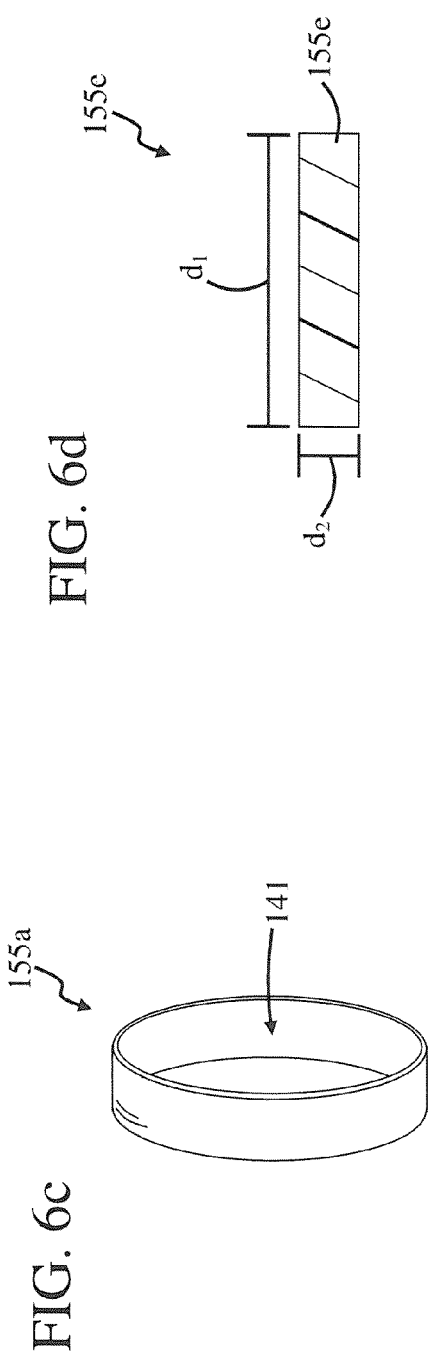
FIG. 6c
FIG. 6d

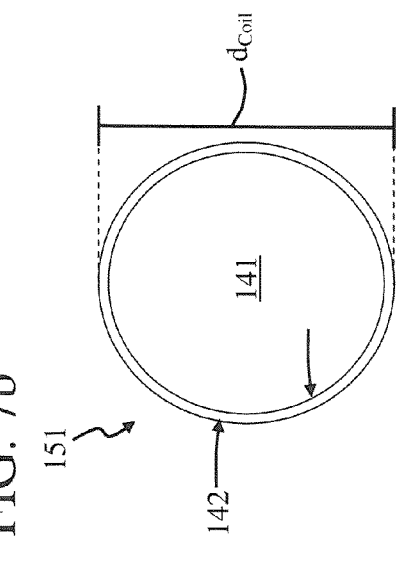
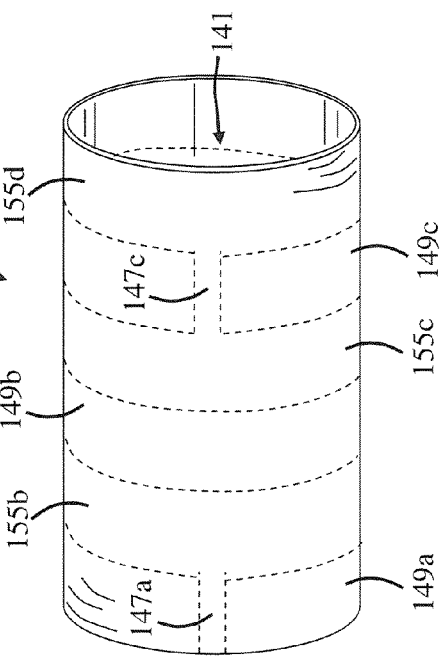
FIG. 7b
FIG. 7d
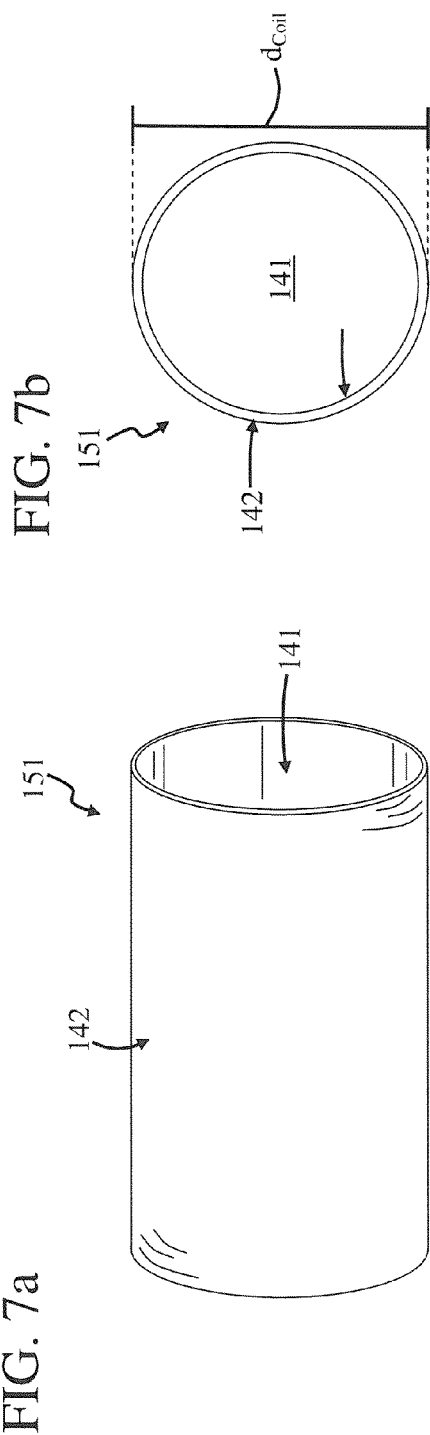
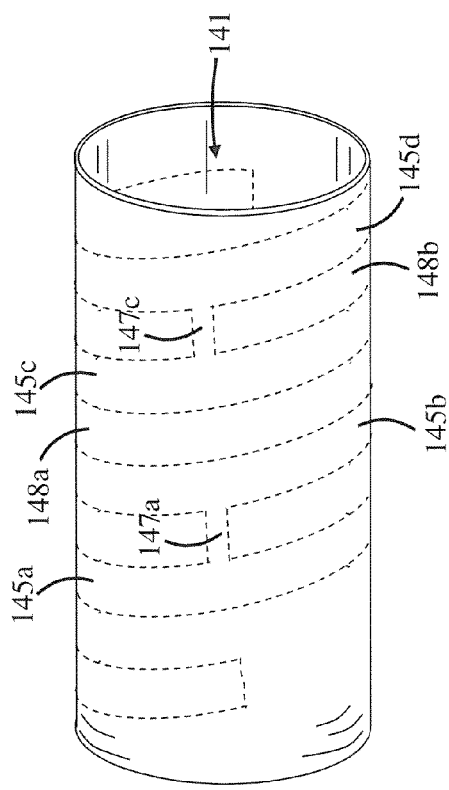
FIG. 7a
FIG. 7c

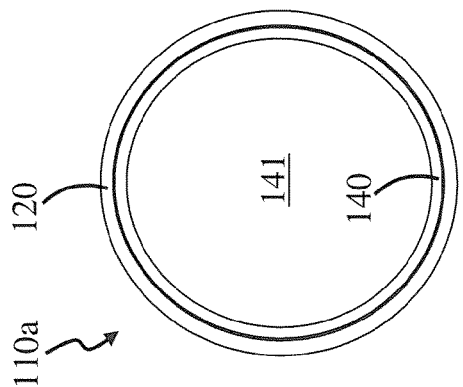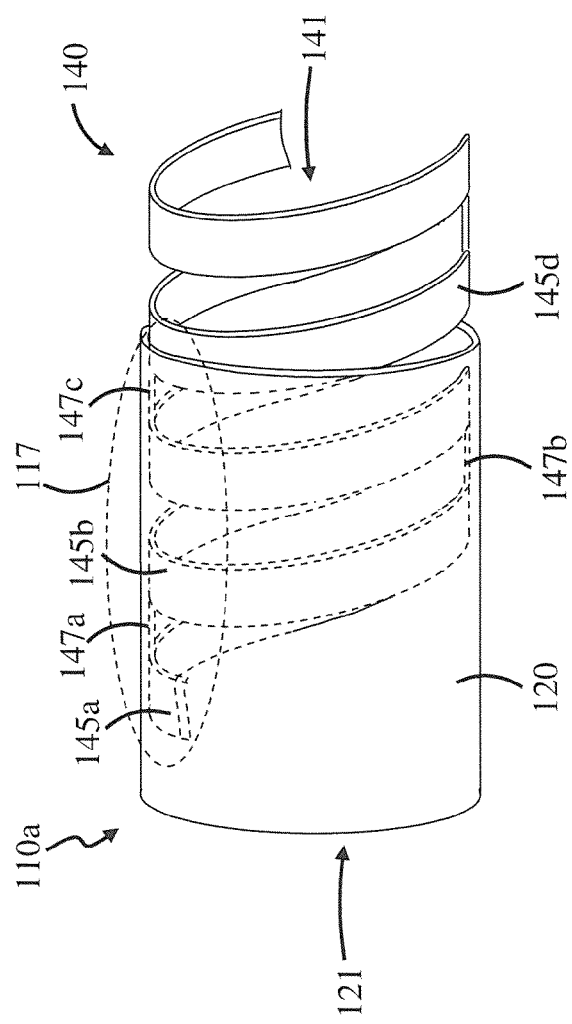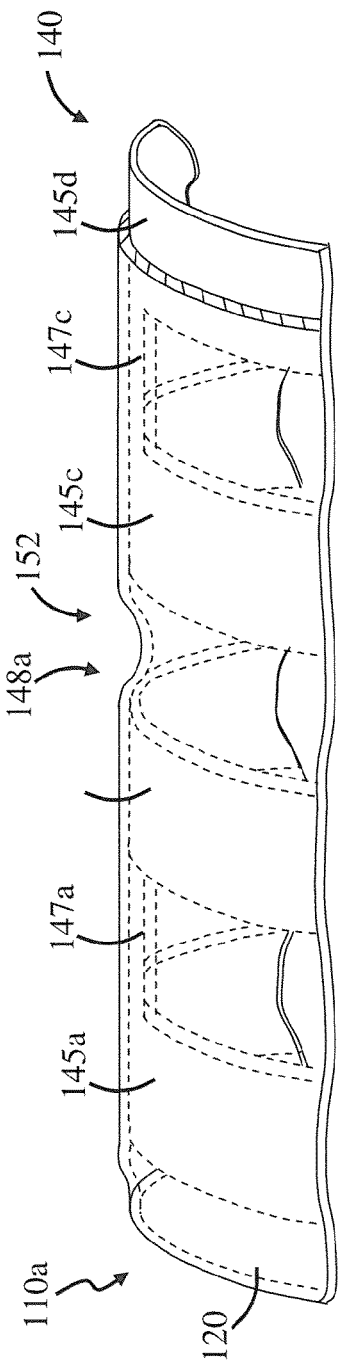

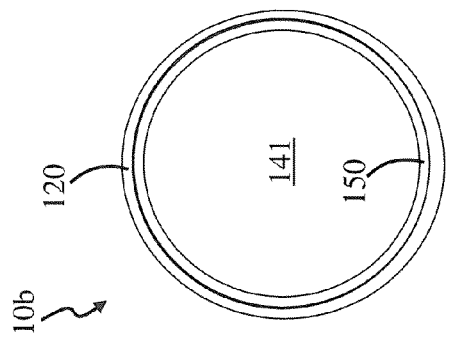
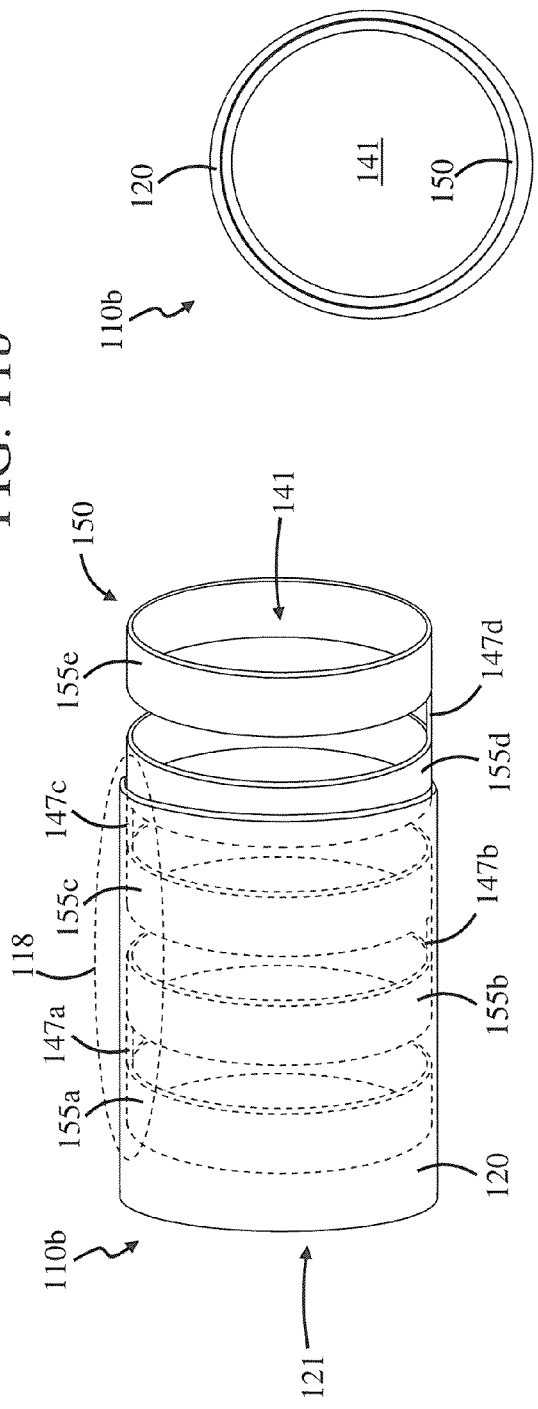
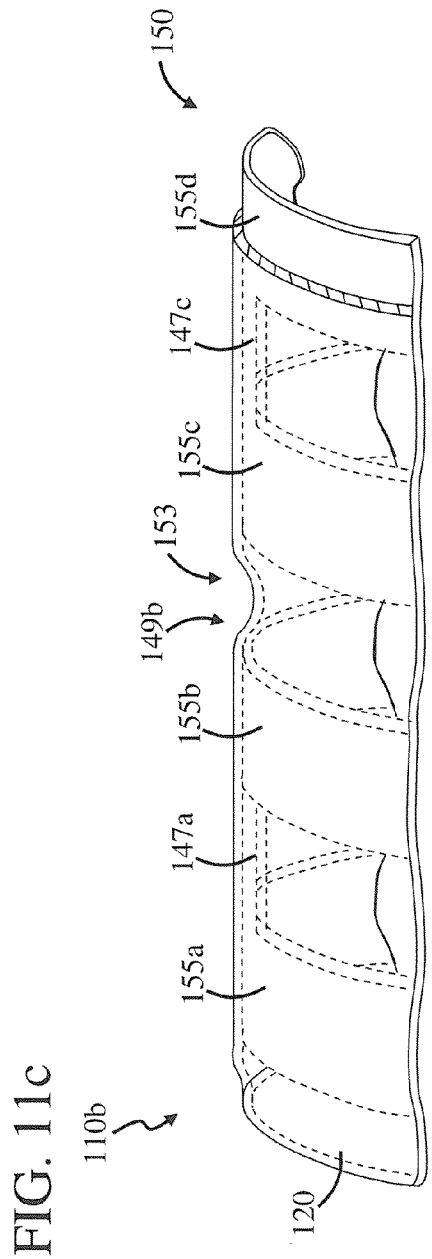
FIG. 11b
FIG. 11a
FIG. 11c

CATHETER AND METHOD OF MAKING THE SAME

CROSS-REFERENCE TO RELATED APPLICATIONS

This application is a Non-Provisional of U.S. Provisional Application No. 61/218,355, filed on Jun. 18, 2009, the contents of which are incorporated herein by reference in their entirety.

BACKGROUND OF THE INVENTION

1. Field of the Invention

This invention relates generally to medical devices, such as catheters, and particularly to enteral feeding catheters.

2. Description of the Related Art

Feeding-decompression catheters must reside within the gastrointestinal (G-I) tract of patients for prolonged periods. A catheter may be delivered by direct penetration through the abdominal and gastrointestinal walls. Some directly placed catheters may then be directed to traverse the normal G-I channels to reach a more distal duodenal or jejunal feeding and/or aspiration site.

Alternatively, the catheter may be introduced indirectly and less traumatically into the body through a natural opening (e.g., nasal passage), to then traverse the natural G-I channels to the gastric or intestinal feeding and/or aspiration site. As the catheter encounters sharp bends and makes prolonged contact, it may irritate sensitive tissue. The size of the nasal passage and ever increasing discomfort limit the maximum outside diameter (O.D.) of a useful nasal catheter to about 6.7 mm, or about 20 Fr (French) units, wherein 3 Fr units=1 mm.

Some catheters are single lumen catheters and others are dual lumen devices which include feeding and aspirating tubes. Such single and dual lumen catheters are disclosed in U.S. Pat. Nos. 3,618,613, 4,543,089, 4,642,092, 4,705,511, 4,806,182, 5,334,169, 5,520,662, 5,599,325, 5,676,659, 5,807,311, 5,947,940, 6,508,804, 6,659,974, 6,881,211, 6,921,396 and 6,949,092, the contents of which are incorporated entirely herein by reference.

The O.D. of all feeding devices must be minimized to reduce patient trauma and discomfort. The catheter must provide necessary clearances to accommodate feeding inflow and/or aspirate outflow, while also minimizing the likelihood of blockage.

The internal diameter (I.D.) of a feeding channel required to accommodate an adequate flow rate by gravity feed or by pump can be met easily. However, the adequacy of aspiration flow is less certain. The volume of aspirate to be removed fluctuates, and often exceeds many-fold the rate of feeding. Excess digestive juices and swallowed air that escape removal may be propelled downstream, to accumulate and cause distention. Further, the aspiration channel is at greater risk for occlusion by the particulates and mucus encountered in the gastrointestinal fluids. The I.D. of the aspiration channel, especially, must be maximized.

The enteral feeding catheter is used to provide patients with nourishment, utilizing the propulsion and absorption functions of the gastrointestinal tract. Adequate food nourishes the patients, accelerates healing, aids infection resistance, and decreases recovery time. However, G-I motility of hospitalized patients is characteristically impaired by disease and/or trauma, including the trauma incident to surgery.

An aspirating tube is positioned proximal to the feeding site to reduce abdominal distention, which occurs when air and excess fluids accumulate. The aim of this aspiration is to intercept all swallowed air, and also remove any inflowing liquid that exceeds the patient's capacity for outflow via peristalsis from the feeding site. The outer layer of the aspirating catheter must allow for inflow of fluid, between the coils of the spring band. If the inner skeleton (the spiral spring band) was overlaid with a layer of continuous plastic, multiple holes will have to be provided by punching, laser drilling, etc.

Abdominal distention exerts its harmful effects in several ways. It reduces the ability of the patient to adequately breathe deeply, cough and clear secretions, predisposing to pneumonia. It causes extreme discomfort and limits mobility. It interferes with nutrient absorption. The resulting undernourishment slows the healing process, reduces the patient's optimum resistance to infection, and increases the recovery time.

When a catheter is inserted via the nose, it bends to conform to the nasal passage, esophagus, etc. The bent catheter may kink, causing partial or total occlusion. This is prevented in standard catheters by increasing the thickness of the flexible wall.

One example of such a current feeding tube from CR Bard, Inc. is a gastrostomy catheter for direct placement into the stomach. It has an I.D. of 6 mm and an O.D. of 9.3 mm, or 28 Fr units. The wall thickness of 1.67 mm (5 Fr units) is designed to prevent kinking. A 28 Fr catheter is too large and uncomfortable to insert transnasally in a patient. The nasal catheters in current use are necessarily more slender, and therefore have lumens with compromised functionality.

Therefore, it is an object of the present invention to provide a catheter with an ultra-thin wall that is less likely to experience kinking in response to being bent.

BRIEF SUMMARY OF THE INVENTION

Embodiments of the present invention provide a catheter, and methods of manufacturing and using the catheter.

In one embodiment, a slender device that is both flexible and kink resistant is provided. The catheter is made of a thin wall, biocompatible plastic elastomer, such as but not limited to polyurethane, reinforced with a thin helical spring band, such as but not limited to a thin helical spring band of stainless steel. The total wall thickness of a 6 mm I.D. catheter made in accordance with the present invention can be less than about $\frac{1}{30}^{th}$ of its O.D.

The reinforcing spring band may be made in two layers, as double, overlapping helices. Each of the plies will be less than half the thickness required by a single-layered spring for the same structural strength.

Simple liquid flow through a gastrointestinal catheter is generally proportional to the $4^{th}$ power of the I.D. The likelihood of occlusion is not so easily defined, but may reach a similar (or greater) value under encountered circumstances. Even modest increase in the I.D. profoundly improves flow rate and occlusion resistance.

In another embodiment, a fine cloth mesh sleeve, such as, but not limited to polyester, nylon, or a mixture thereof, tightly encases the otherwise exposed distal helical spring band is utilized. The fine cloth mesh sleeve is generally about 0.002" thick, This allows free inflow of the gastric and intestinal liquids surrounding that section of the catheter, and provide longitudinal stability. The impervious plastic layer will overlay the proximal portion of the spring band, with an approximately one inch of overlap to secure the cloth mesh sleeve in place. The terminal end of the sleeve can be secured to the terminal end of the spring band with adhesive or by other mechanical means.

In still another embodiment, this cloth mesh sleeve will encase the entire length of underlying helical spring band. An extremely thin layer, about 0.00025" of heat shrinkable polyester or polyolefin tubing can be applied to overlay the proximal segment of the catheter, making it impervious to fluid. Heat shrink tubing usually imparts a relative inflexibility to the underlying material. By making this heat shrink tubing ultra-thin, adequate flexibility is achieved. However, this layer may be at risk for "cutting" by the underlying stainless steel spring band. The cloth mesh sleeve between the heat shrink tubing and spring band would protect the former while minimizing the thickness.

The novel features of these embodiments are set forth with particularity in the appended claims. The invention will be best understood from the following description when read in conjunction with the accompanying drawings.

BRIEF DESCRIPTION OF THE DRAWINGS

FIGS. 5a, 5b and 5c are perspective, side and end views, respectively, of the reinforcement member of FIG. 1 embodied as a helical reinforcement member.

FIG. 5e is a sectional view of the helical reinforcement member of FIGS. 5a, 5b and 5c taken along a cut-line 5e-5e of FIG. 5a.

FIG. 5p is a side view of another embodiment of a helical reinforcement member, which can be included with the catheter of FIG. 1.

FIGS. 6a and 6b are perspective and end views, respectively, of a non-helical reinforcement member, which can be included with the catheter of FIG. 1.

FIG. 6c is a perspective view of a non-helical band coil of the non-helical reinforcement member of FIGS. 6a and 6b.

FIG. 6d is a sectional view of the non-helical reinforcement member of FIGS. 6a and 6b taken along a cut-line 6d-6d of FIG. 6a.

FIGS. 7a and 7b are perspective and end views, respectively, of a resilient reinforcement member tube with a reinforcement member channel extending therethrough.

FIG. 7c is a perspective view of the resilient reinforcement member tube of FIGS. 7a and 7b showing the helical reinforcement member of FIGS. 5a, 5b and 5c in phantom.

FIG. 7d is a perspective view of the resilient reinforcement member tube of FIGS. 7a and 7b showing the non-helical reinforcement member of FIGS. 6a and 6b in phantom.

FIG. 8c is a cut-away side view of the vacuum tube system of FIGS. 8a and 8b taken along a cut-line 8c-8c of FIG. 8a.

FIGS. 10a and 10b are perspective and end views, respectively, of a catheter, wherein the helical reinforcement member of FIGS. 5a and 5b is shown as partially extending through the resilient tube of FIGS. 3a and 3b.

FIG. 10c is a close-up view of the catheter of FIGS. 10a and 10b.

FIGS. 11a and 11b are perspective and end views, respectively, of a catheter, wherein the non-helical reinforcement member of FIGS. 6a and 6b is shown as partially extending through the resilient tube of FIGS. 3a and 3b.

FIG. 11c is a close-up view of the catheter of FIGS. 11a and 11b.

FIG. 12b is a side view of the non-helical reinforcement member of FIG. 12a.

FIGS. 12c and 12d are perspective views of the resilient tube of FIG. 12a looking in directions indicated in FIG. 12a.

DETAILED DESCRIPTION OF THE INVENTION

Figure 1:
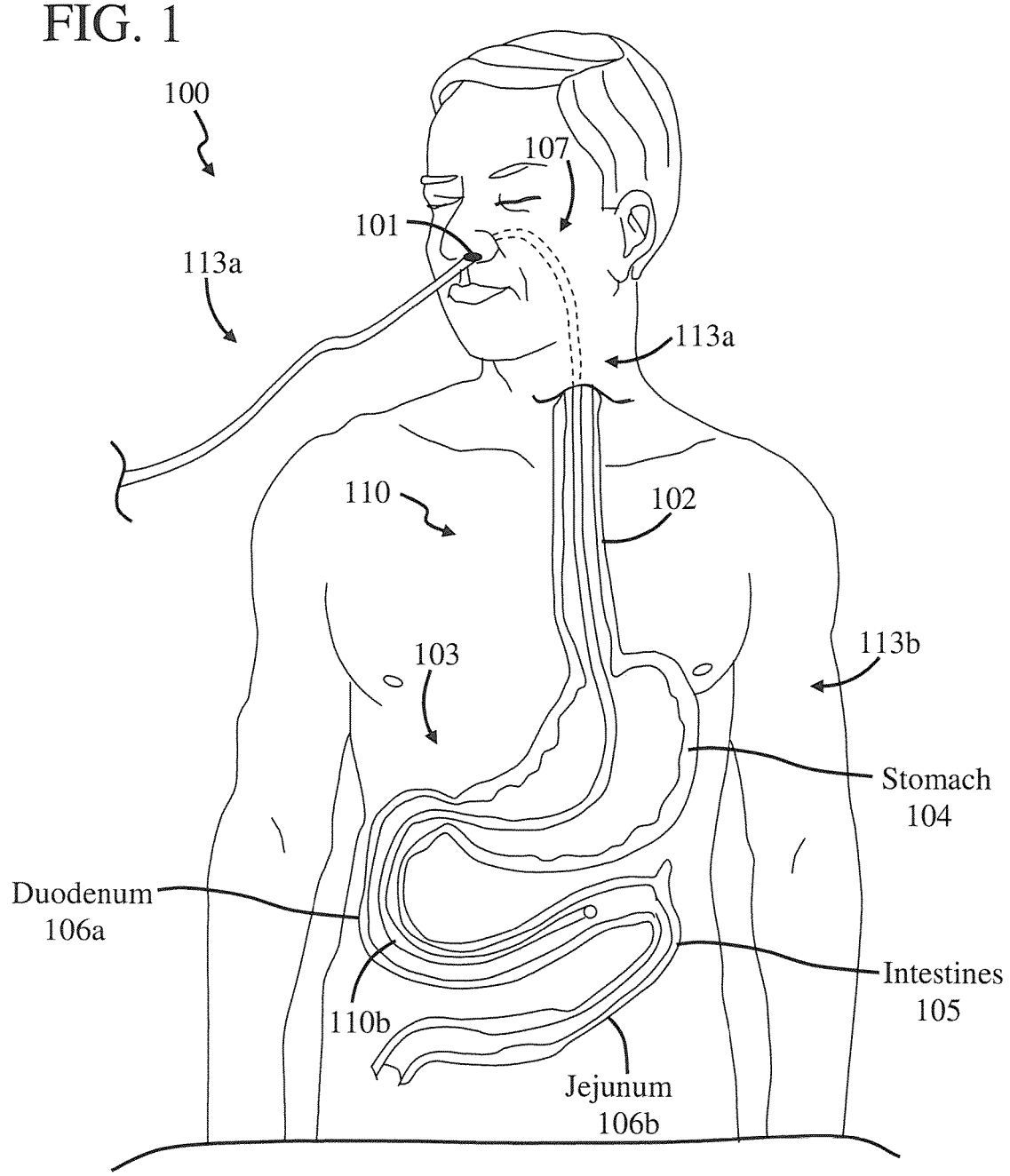
FIG. 1 is a front view of a person with a catheter inserted therein, wherein the catheter includes a resilient tube and reinforcement member.

FIG. 1 is a front view of a person 100 with a catheter 110 inserted therein. It should be noted that catheter 110 can be used as many different medical devices, such as a feeding tube, aspirating tube, etc. Further, catheter 110 includes a single lumen in this embodiment, but it can include more than one lumen, if desired. An embodiment of catheter 110 which includes two lumens is often referred to as a dual lumen catheter. One example of a dual lumen catheter includes feeding and aspirating tubes, wherein the feeding tube extends through the aspiration tube. The feeding tube is positioned distal to but in close proximity (<5 cm) to the end of the aspiration tube, but still within the same anatomical segment of the G-I tract, e.g the duodenum. More information regarding dual lumen devices can be found in the references cited in the Background.

In this embodiment, catheter 110 has been positioned so it extends through a nasal passage 101 of person 100 and esophagus 102 and into the gastrointestinal tract 103. Catheter 110 extends between nasal passage 101 and gastrointestinal tract 103, and is bent in a region 107 of person 100. It should be noted that gastrointestinal tract 103 includes stomach 104 and intestines 105 of person 100. Further, intestines 105 of person 100 include a duodenum 106a and jejunum 106b. The proximal portion of catheter 110, denoted as proximal portion 113a, is proximate to nasal passage 101. Further, the distal portion of catheter 110, denoted as distal portion 113b, extends through esophagus 102 and into gastrointestinal tract 103. In particular, distal portion 113b extends into duodenum 106a or jejunun 106b. As discussed in more detail below, catheter 110 is resistant to kinking when it is inserted through nasal passage 101 and esophagus 102 and into gastrointestinal tract 103.

Figure 2:
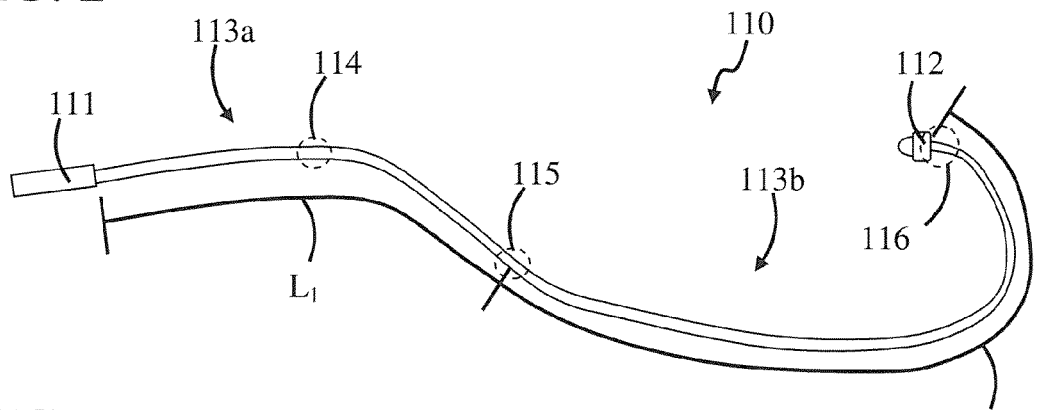
FIG. 2 is a side view of the catheter of FIG. 1.

FIG. 2 is a side view of catheter 110. In this embodiment, catheter 110 includes a connector 111 with a side-arm 111a connected to proximal portion 113a, and a tip 112 connected to distal portion 113b. Connector 111 allows catheter 110 to be operatively connected to a machine (not shown), such as a feeding or aspirating machine, and tip 112 retains portion 113b in gastrointestinal tract 103. The machine controls the flow of material through catheter 110 and between nasal passage 101 and gastrointestinal tract 103. In this way, catheter 110 is operatively connected to the machine. In this embodiment, the material includes gastric and intestinal juices and food.

As shown in FIG. 2, proximal portion 113a and distal portion 113b have lengths $L_1$ and $L_2$, respectively. Lengths $L_1$ and $L_2$ can have many different values. For example, in one embodiment, length $L_1$ is between about eight inches to about fifteen inches, and length $L_2$ is between about thirty inches to about forty inches. It is desirable for proximal portion 113a to be able to extend through nasal passage 101 and esophagus 102 without kinking, such as in region 107 (FIG. 1). Further, it is desirable for distal portion 113b to be allowed to bend, but limited stretching and compressing.

As will be discussed in more detail below, catheter 110 includes a resilient tube of material having a channel, and a reinforcement member which extends through the channel. The resilient tube extends between proximal portion 113a and distal portion 113b. The length of the resilient tube is chosen so it can extend through nasal passage 101 and into gastrointestinal tract 103 (FIG. 1). The resilient tube channel extends along the length of the resilient tube. Hence, the resilient tube channel extends through proximal portion 113a and distal portion 113b.

The resilient tube can be manufactured in many different ways. For example, the resilient tube can be manufactured by rolling flat pieces of resilient material into tubes. The resilient tube also be extruded. The resilient tube can be extruded in many different ways, such as those disclosed in U.S. Pat. Nos. 4,791,965, 4,888,146, 5,102,325, 5,542,937, 6,045,547, 6,165,166, 6,434,430, 6,692,804, 6,773,804 and 6,776,945, the contents of which are incorporated herein by reference.

The reinforcement member extends along the length of the resilient tube. In some embodiments, the reinforcement member extends through proximal portion 113a and not through distal portion 113b. In other embodiments, the reinforcement member extends through distal portion 113b and not through proximal portion 113a. In some embodiments, the reinforcement member extends through proximal portion 113a and distal portion 113b.

The reinforcement member is allowed to bend. A reinforcement member is allowed to bend when it is allowed to move side-to-side. Further, a reinforcement member is allowed to bend when it is allowed to flex. A reinforcement member is restricted from bending when it is restricted from moving side-to-side. Further, a reinforcement member is restricted from bending when it is restricted from flexing. It should be noted that catheter 110 is bent in FIGS. 1 and 2. Further, the reinforcement member (not shown) of catheter 110 is bent in FIGS. 1 and 2.

The reinforcement member is allowed to bend so it can extend through nasal passage 101 and esophagus 102 and reduce the likelihood of the resilient tube being kinked. The flow of material through the resilient tube can be undesirably restricted when the resilient tube kinks. The reinforcement member is allowed to bend so it can extend through nasal passage 101 and esophagus 102 and reduce the likelihood of the resilient tube channel kinking. The flow of material through the resilient tube channel can be undesirably restricted when the resilient tube channel kinks.

In some embodiments of catheter 110, the reinforcement member is restricted from stretching. A reinforcement member is restricted from stretching when its length is restricted from increasing. A reinforcement member is allowed to stretch when its length is allowed to increase. In some of these embodiments, the reinforcement member is restricted from compressing. The reinforcement member is restricted from compressing when its length is restricted from decreasing. The reinforcement member is allowed to compress when its length is allowed to decrease.

Figure 3A:
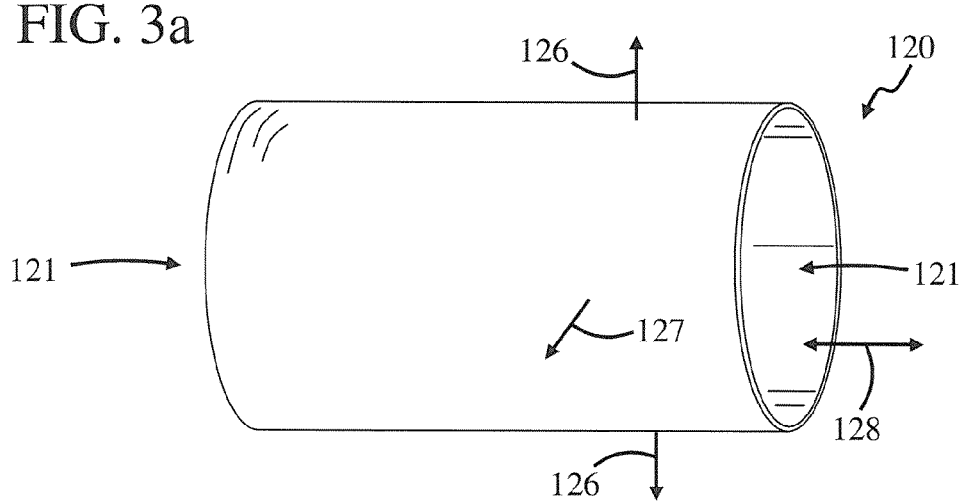
FIGS. 3a and 3b are perspective and end views, respectively, of a portion of the resilient tube of FIG. 1.
Figure 3B:
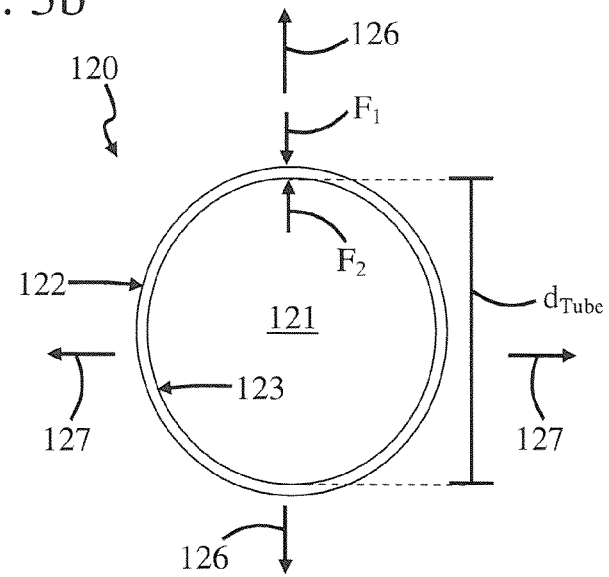

FIGS. 3a and 3b are perspective and end views, respectively, of a portion of a resilient tube 120, which is included with catheter 110. The portion of resilient tube 120 shown in FIG. 3a can be the portion of resilient tube 120 extending through a region 114 of catheter 110, which is shown in FIG. 2. Region 114 can be any portion of proximal portion 113a. The portion of resilient tube 120 shown in FIG. 3a can be the portion of resilient tube 120 extending through a region 115 of catheter 110, which is shown in FIG. 2. Region 115 includes a portion of proximal portion 113a and distal portion 113b. The portion of resilient tube 120 shown in FIG. 3a can be the portion of resilient tube 120 extending through a region 116 of catheter 110, which is shown in FIG. 2. Region 116 can be any portion of distal portion 113b.

In this embodiment, resilient tube 120 has a tube channel 121, and an outer resilient tube surface 122 and inner resilient tube surface 123, all of which extend along its length. Inner resilient tube surface 123 faces tube channel 121 and outer resilient tube surface 122 faces away from tube channel 121. It should be noted that outer resilient tube surface 122 and inner resilient tube surface 123 are annular surfaces which extend around tube channel 121. Further, outer resilient tube surface 122 and inner resilient tube surface 123 are curved surfaces which curve around tube channel 121.

The material of tube 120 is chosen so that resilient tube 120 can be stretched and compressed in a direction 128 in FIG. 3a, wherein direction 128 extends along the length of resilient tube 120. The material of tube 120 is chosen so that resilient tube 120 can be bent, as indicated by direction arrows 126 and 127 in FIGS. 3a and 3b. It should be noted that directions 126 and 127 are perpendicular to each other, and directions 126 and 127 are perpendicular to direction 128.

The material of tube 120 is chosen so that outer resilient tube surface 122 and inner resilient tube surface 123 are both collapsible in response to a force $F_1$ applied to outer resilient tube surface 122 (FIG. 3b). It should be noted that a dimension $d_{Tube}$ of channel 121 decreases in response to force $F_1$ being applied to outer resilient tube surface 122. In this embodiment, dimension $d_{Tube}$ corresponds to an inner diameter of tube channel 121. Dimension $d_{Tube}$ of channel 121 extends between opposed sides of inner resilient tube surface 123. Dimension $d_{Tube}$ can have many different values. In one embodiment, dimension $d_{Tube}$ has a value in a range between about 0.100 inches to about 0.500 inches.

The material of resilient tube 120 can be of many different types, such as polyurethane, polysiloxane, and polyfluorohydrocarbons ("TEFLON"). It should be noted that resilient materials are often referred to as elastomers. Examples of materials which can be used in resilient tube 120 are disclosed in some of the patents referenced in the background of this application. It should also be noted that resilient tube 120 includes a single layer of resilient material in the shape of a tube. However, resilient tube 120 generally includes one or more layers of resilient material in the shape of a tube.

The resilient material is chosen so that outer resilient tube surface 122 and inner surface 123 are both stretchable in response to a force $F_2$ applied to inner resilient tube surface 123 (FIG. 3b). It should be noted that dimension $D_{Tube}$ of channel 121 increases in response to force $F_2$ being applied to inner resilient tube surface 123. The resilient material is chosen so that outer resilient tube surface 122 and inner surface 123 are both repeatably moveable between stretched and unstretched conditions.

It is useful to be able to increase the value of dimension $D_{Tube}$ so that the reinforcement member can be extended through resilient tube channel 121, as will be discussed with FIG. 9c. Dimension $D_{Tube}$ of channel 121 increases in response to force $F_2$ being increased and force $F_1$ being decreased. Dimension $D_{Tube}$ of resilient tube channel 121 decreases in response to force $F_2$ being decreased and force $F_1$ being increased. It is useful to be able to decrease the value of dimension $D_{Tube}$ so that inner resilient tube surface 123 can be moved towards the reinforcement member extending through resilient tube channel 121, as will be discussed with FIG. 9d.

The reinforcement member of catheter 110 can be of many different types. For example, in some embodiments, the reinforcement member of catheter 110 is a helical reinforcement member and, in other embodiments, the reinforcement member of catheter 110 is a non-helical reinforcement member.

Figure 4B:
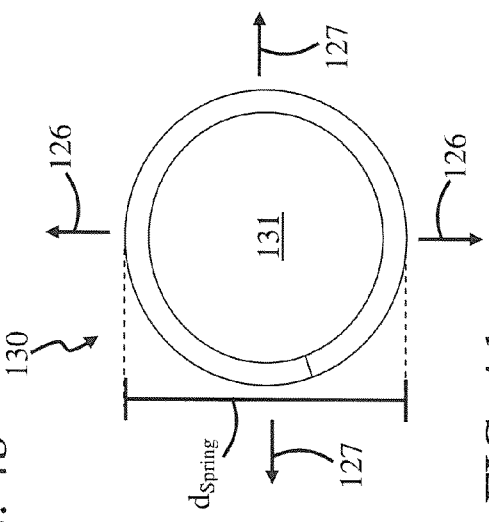
FIGS. 4a, 4b and 4c are side, end and perspective views, respectively, of the reinforcement member of FIG. 1 embodied as a helical spring.
Figure 4D:
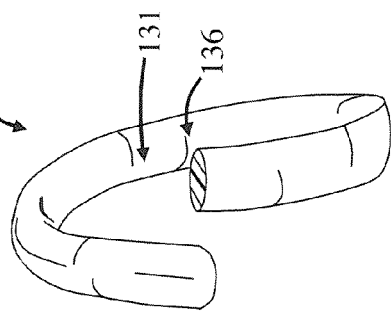
FIG. 4d is a perspective view of a helical coil of the helical spring of FIGS. 4a, 4b and 4c.
Figure 4A:
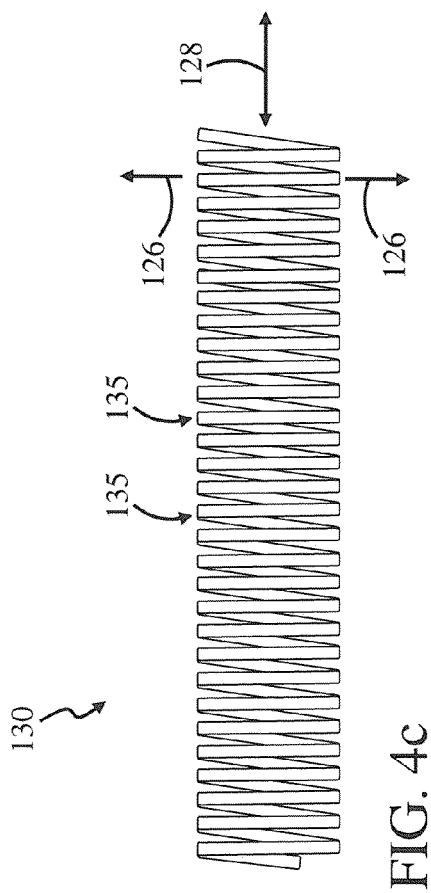
Figure 4C:
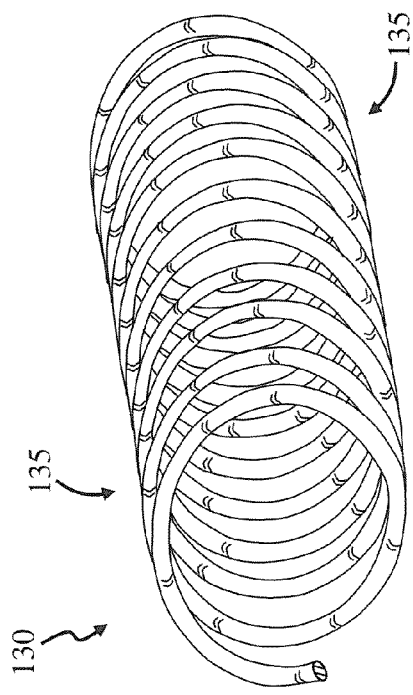

FIGS. 4a, 4b and 4c are side, end and perspective views, respectively, of a helical reinforcement member embodied as a helical spring 130 having a helical spring channel 131 extending therethrough. In this embodiment, helical spring 130 is allowed to bend in directions 126 and 127, and to stretch and compress in direction 128. Helical spring 130 has an outer dimension, which is denoted as dimension $d_{Spring}$. In this embodiment, outer dimension $d_{Spring}$ corresponds to the outer diameter of helical spring 130. Dimension $d_{Spring}$ can have many different values. In one embodiment, dimension $d_{Spring}$ has a value in a range between about 0.100 inches to about 0.500 inches. In other embodiments, dimension $d_{Spring}$ has a value in a range between about 0.200 inches to about 0.500 inches.

Helical spring 130 includes a number of helical coils 135, wherein one helical coil 135 is shown in a perspective view of FIG. 4d. The helical coils of helical spring 130 are coupled together in a well-known manner so they operate as a spring. In particular, the helical coils of helical spring 130 are coupled together so helical spring 130 is allowed to compress, stretch and bend. In this way, the helical coils of helical spring 130 are coupled together so they operate as a spring.

It should be noted that outer dimension $d_{Spring}$ corresponds to the outer diameter of helical coil 135. It should also be noted that helical spring 130 generally includes a single elongate piece of material that has a helical shape. Hence, the helical coils of helical spring 130 can correspond to coils of the single elongate piece of material.

In this embodiment, helical coil 135 has a circular cross-sectional shape, as seen in FIG. 4d, and as indicated by an indication arrow 136. Hence, the cross-sectional shape of helical coil 135 is not band-shaped. Examples of band-shaped helical coils will be discussed in more detail below. Helical spring 130 can be manufactured in many different ways, such as those disclosed in U.S. Pat. Nos. 4,302,959, 5,363,681, 6,006,572, 6,923,034 and 7,198,187.

FIGS. 5a, 5b and 5c are perspective, side and end views, respectively, of a helical reinforcement member 140. As discussed in more detail below, helical reinforcement member 140 is allowed to bend in directions 126 and 127, and is restricted from stretching and compressing in direction 128 (FIG. 5b). Helical reinforcement member 140 has an outer dimension, which is denoted as dimension $d_{Coil}$ in FIG. 5c. In this embodiment, outer dimension $d_{Coil}$ corresponds to the outer diameter of helical reinforcement member 140. Dimension $d_{Coil}$ can have many different values. In one embodiment, dimension $d_{Coil}$ has a value in a range between about 0.100 inches to about 0.500 inches. In other embodiments, dimension $d_{Coil}$ has a value in a range between about 0.200 inches to about 0.500 inches.

As shown in FIG. 5c, helical reinforcement member 140 has a reinforcement member channel 141 extending therethrough, and an outer reinforcement member surface 142 and inner reinforcement member surface 143. Inner reinforcement member surface 143 faces reinforcement member channel 141 and outer reinforcement member surface 142 faces away from reinforcement member channel 141. It should be noted that outer reinforcement member surface 142 and inner reinforcement member surface 143 are annular surfaces which extend around reinforcement member channel 141. Further, outer reinforcement member surface 142 and inner reinforcement member surface 143 are curved surfaces which curve around reinforcement member channel 141.

Figure 5E:
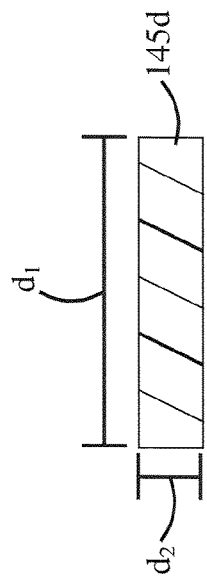
Figure 5D:
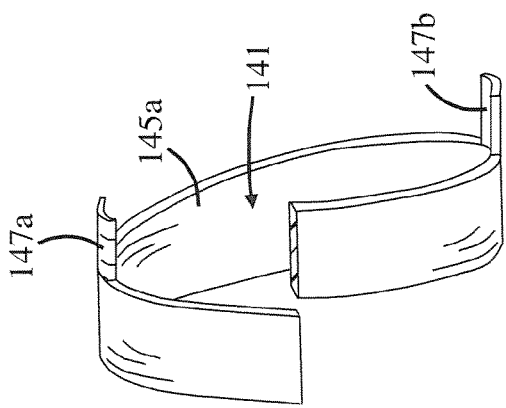
FIG. 5d is a perspective view of a helical band coil of the helical reinforcement member of FIGS. 5a, 5b and 5c.

In this embodiment, helical reinforcement member 140 includes a number of helical band coils 145a, 145b, 145c, 145d and 145e, wherein helical band coil 145a is shown in a perspective view in FIG. 5d. Helical band coils 145a, 145b, 145c, 145d and 145e are coupled together so helical reinforcement member 140 has a helical shape. It should be noted that reinforcement member channel 141 extends through helical band coils 145a, 145b, 145c, 145d and 145e. It should also be noted that the outer diameter of helical band coils 145a, 145b, 145c, 145d and 145e correspond to dimension $d_{Coil}$.

In this embodiment, helical reinforcement member 140 includes a single elongate piece of material which has a helical shape. Hence, the helical band coils of helical reinforcement member 140 correspond to coils of the single elongate piece of material.

FIG. 5e is a sectional view of helical reinforcement member 140 taken along a cut-line 5e-5e of FIG. 5a. In particular, FIG. 5e is a sectional view of helical band coil 145d taken along cut-line 5e-5e of FIG. 5a. In this embodiment, helical band coil 145d is band-shaped because its cross-sectional width, denoted as dimension $d_1$ in FIG. 5e, is greater than its cross-sectional thickness, denoted as dimension $d_2$. Helical band coil 145d does not have a circular cross-sectional shape as does helical spring 130, as shown in FIG. 4d. It should be noted that helical band coils 145a, 145b, 145c and 145e also have cross-sectional dimensions $d_1$ and $d_2$ because, as mentioned above, the helical band coils of helical reinforcement member 140 correspond to coils of the single elongate piece of material. In this way, helical reinforcement member 140 includes a single elongate band-shaped piece of material having a width that is greater than its thickness.

Dimensions $d_1$ and $d_2$ can have many different values. In one embodiment, dimension $d_1$ has a value between about 0.001 inches to about 0.250 inches, and dimension $d_2$ has a value between about 0.0005 inches to about 0.010 inches.

In this embodiment, helical reinforcement member 140 includes a number of arms 147a, 147b, 147c and 147d, which restrict the ability of helical reinforcement member 140 to stretch and compress in direction 128, and allow helical reinforcement member 140 to bend in directions 126 and 127. Arms 147a-g are optional. Arm 147a is connected between upper portions of helical band coils 145a and 145b and arm 147b is connected between lower portions of helical band coils 145a and 145b. Arms 147a and 147b are shown connected to upper and lower portions of helical band coil 145a in FIG. 5d. Arm 147c is connected between upper portions of helical band coils 145c and 145d, and arm 147d is connected between lower portions of helical band coils 145c and 145d.

It should be noted that upper and lower portions of some of the helical coils of helical reinforcement member 140 are not coupled together with arms so that there is a gap therebetween. For example, as shown in FIG. 5b, a gap 148a extends between the upper portion of reinforcement member 140 between helical band coils 145b and 145c. Further, a gap 148b extends between the lower portion of reinforcement member 140 between helical band coils 145c and 145d. Gaps 148a and 148b allow helical band coils 145c and 145d to bend in directions 126 and 127. It should be noted that, in this embodiment, gaps 148a and 148b extend annularly around reinforcement member channel 141. Further, gaps 148a and 148b extend helically around reinforcement member channel 141. Gaps 148a and 148b extend helically around reinforcement member channel 141 because band coils 145c and 145d are helical band coils. In this way, gaps 148a and 148b are helical gaps.

Figure 5F:
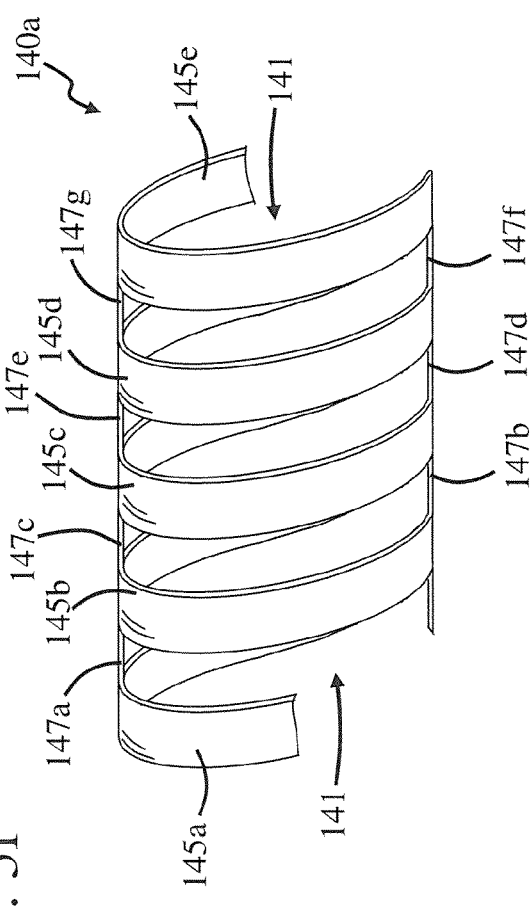
FIG. 5f is a perspective view of another embodiment of a helical reinforcement member, which can be included with the catheter of FIG. 1.

An example of a helical reinforcement member, denoted as helical reinforcement member 140a, which includes arms extending between upper and lower edges of each helical band coils is shown in FIG. 5f. In general, a helical reinforcement member is allowed to bend less as the number of arms extending between the helical band coils increases. A helical reinforcement member is allowed to bend more as the number of arms extending between the helical band coils decreases. Further, a helical reinforcement member is allowed to bend less as the number of gaps extending between the helical band coils increases. A helical reinforcement member is allowed to bend more as the number of gaps extending between the helical band coils decreases. It should be noted that the number of gaps increases and decreases as the number of arms increase and decrease, respectively.

Figure 5G:
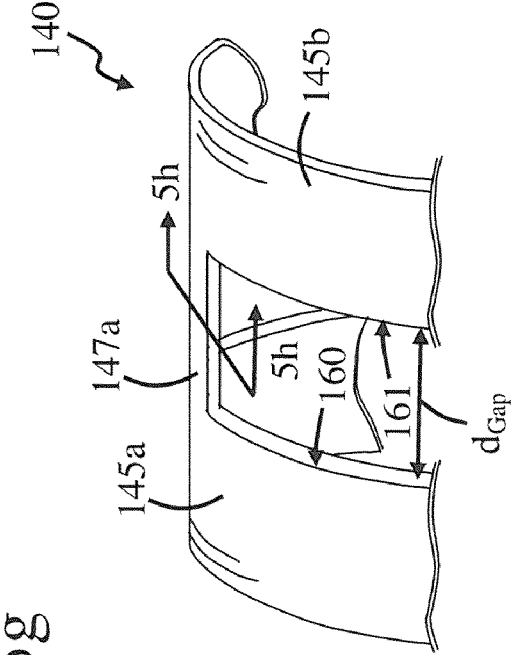
FIG. 5g is a close-up perspective view of the helical reinforcement member of FIGS. 5a, 5b and 5c.
Figure 5H:
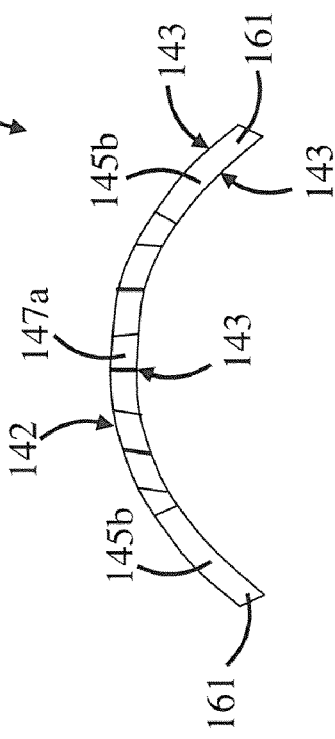
FIG. 5h is a cut-away side view of the helical reinforcement member of FIGS. 5a, 5b and 5c taken along a cut-line 5h-5h of FIG. 5g.
Figure 5I:
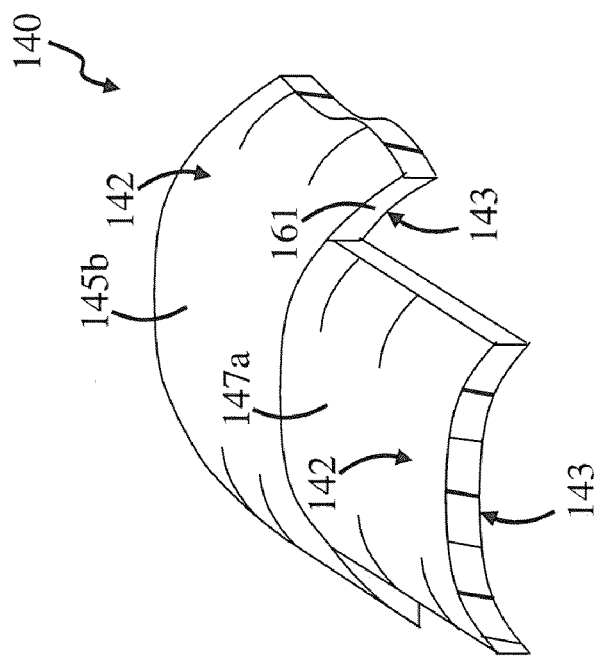
FIG. 5i is a perspective view of the helical reinforcement member of FIGS. 5a, 5b and 5c taken along cut-line 5h-5h of FIG. 5g.

FIG. 5g is a perspective view of helical reinforcement member 140 in a region 144 of FIG. 5a. FIG. 5h is a cut-away side view of helical reinforcement member 140 in region 144 taken along a cut-line 5h-5h of FIG. 5g. FIG. 5i is a perspective view of helical reinforcement member 140 in region 144 taken along cut-line 5h-5h of FIG. 5g.

Arm 147a extends between, and is coupled to, helical band coils 145a and 145b. In this way, helical reinforcement member 140 includes helical band coils coupled together with an arm. Arm 147a restricts the ability of helical band coils 145a and 145b to move towards each other. Hence, arm 147a restricts the ability of helical band coils 145a and 145b to be compressed. Arm 147a restricts the ability of helical band coils 145a and 145b to move away from each other. Hence, arm 147a restricts the ability of helical band coils 145a and 145b to be stretched. In this way, helical reinforcement member 140 includes an arm which restricts the ability of the helical band coils of helical reinforcement member 140 to be stretched and compressed.

Helical band coils 145a and 145b include edges 160 and 161, respectively, which extend along them. Edges 160 and 161 are spaced apart from each other by a distance $d_{Gap}$. Distance $d_{Gap}$ can have many different values. In one embodiment, distance $d_{Gap}$ has a value between about 0.0005 inches to about 0.010 inches. In other embodiments, distance $d_{Gap}$ has a value between about 0.001 inches to about 0.007 inches.

In this embodiment, arm 147a extends between edges 160 and 161. In this way, helical reinforcement member 140 includes an arm which extends between edges of helical band coils. Arm 147a restricts the ability of edges 160 and 161 to move towards each other. Hence, arm 147a restricts the ability of helical band coils 145a and 145b to be compressed. Arm 147a restricts the ability of edges 160 and 161 to move away from each other. Hence, arm 147a restricts the ability of helical band coils 145a and 145b to be stretched. In this way, helical reinforcement member 140 includes an arm which restricts the ability of edges of helical band coils of helical reinforcement member 140 to move towards and away from each other.

In this embodiment, edges 160 and 161 are opposed to each other, and arm 147a extends between them. In this way, helical reinforcement member 140 includes an arm which extends between opposed edges of helical band coils. Arm 147a restricts the ability of opposed edges 160 and 161 to move towards each other. Hence, arm 147a restricts the ability of helical band coils 145a and 145b to be compressed. Arm 147a restricts the ability of opposed edges 160 and 161 to move away from each other. Hence, arm 147a restricts the ability of helical band coils 145a and 145b to be stretched. In this way, helical reinforcement member 140 includes an arm which restricts the ability of opposed edges of helical band coils of helical reinforcement member 140 to be moved towards and away from each other.

Helical band coils 145a and 145b are adjacent to each other because they are adjacent coils. Hence, helical reinforcement member 140 includes an arm connected between adjacent helical band coils. Arm 147a restricts the ability of adjacent helical band coils 145a and 145b to move towards each other. Hence, arm 147a restricts the ability of adjacent helical band coils 145a and 145b to be compressed. Arm 147a restricts the ability of adjacent helical band coils 145a and 145b to move away from each other. Hence, arm 147a restricts the ability of adjacent helical band coils 145a and 145b to be stretched. In this way, helical reinforcement member 140 includes an arm which restricts the ability of adjacent helical band coils of helical reinforcement member 140 to be stretched and compressed.

It should be noted that, in this embodiment, arm 147b extends between opposed edges 160 and 161 of helical band coils 145a and 145b. Hence, arm 147b restricts the ability of edges 160 and 161 to move towards each other. In this way, arm 147b restricts the ability of helical band coils 145a and 145b to be compressed. Arm 147b restricts the ability of edges 160 and 161 to move away from each other. In this way, arm 147b restricts the ability of helical band coils 145a and 145b to be stretched. Hence, helical reinforcement member 140 includes more than one arm which restricts the ability of adjacent helical band coils of helical reinforcement member 140 to move towards and away from each other.

Arms 147c and 147d extend between opposed edges of helical band coils 145c and 145d. Hence, arms 147c and 147d restrict the ability of helical band coils 145c and 145d to move towards each other. In this way, arms 147c and 147d restrict the ability of helical band coils 145c and 145d to be compressed. Arms 147c and 147d restrict the ability of edges 160 and 161 to move away from each other. In this way, arms 147b, 147c and 147d restrict the ability of helical band coils 145c and 145d to be stretched.

It should be noted that helical reinforcement member 140 stretches in response to one or more of its helical band coils stretching. Hence, arms 147a, 147b, 147c and 147d restrict the ability of helical reinforcement member 140 to stretch because they restrict the ability of the helical band coils of helical reinforcement member 140 to stretch. Hence, helical reinforcement member 140 includes an arm which restricts it from stretching.

Further, helical reinforcement member 140 compresses in response to one or more of its helical band coils compressing. Hence, arms 147a, 147b, 147c and 147d restrict the ability of helical reinforcement member 140 to compress because they restrict the ability of the helical band coils of helical reinforcement member 140 to compress. Hence, helical reinforcement member 140 includes an arm which restricts it from compressing. In this way, helical reinforcement member 140 includes an arm which restricts the ability of the helical band coils of helical reinforcement member 140 to stretch and compress.

It should be noted that, in some embodiments, helical reinforcement member 140 includes some helical band coils which are coupled to adjacent helical band coils through one or more arms. For example, FIG. 5j is a perspective view of helical band coil 145a. In this embodiment, arms 147a, 147e and 147f extend outwardly from edges of helical band coil 145a, and are coupled to adjacent helical band coils, which are not shown for simplicity.

Figure 5K:
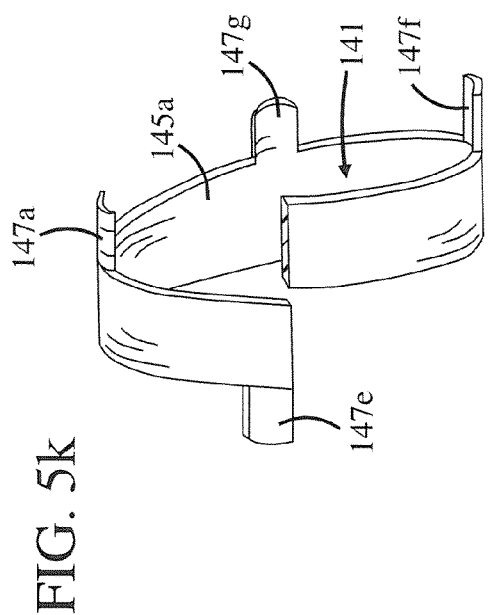
FIG. 5k is a perspective view of the helical band coil of the helical reinforcement member of FIGS. 5a, 5b and 5c having four arms connected thereto.

FIG. 5k is a perspective view of helical band coil 145a. In this embodiment, arms 147a, 147e, 147f and 147g extend outwardly from edges of helical band coil 145a, and are coupled to adjacent helical band coils, which are not shown for simplicity.

It should be noted that some reinforcement members include non-helical band coils that have the same or a different cross-sectional dimension $d_1$ than the others coils of the reinforcement member. For example, FIG. 5l is a perspective view of a reinforcement member, denoted as reinforcement member 140b, which includes helical reinforcement member 140, as discussed in more detail above. Reinforcement member 140b includes a helical band coil 145f coupled to helical band coil 145e, and a non-helical band coil 146 coupled to helical band coil 145f. Non-helical band coil 146 is non-helical because it is ring shaped and not helically shaped, as in helical band coils 145a-145e. More information regarding reinforcement members which include non-helical band coils is provided below with the discussion of FIGS. 6a-6i.

Figure 5M:
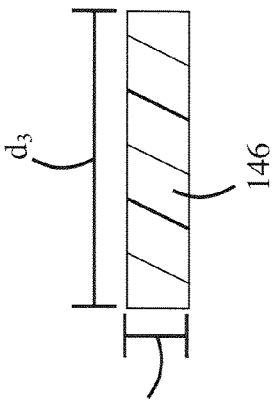
FIG. 5m is a sectional view of the non-helical band coil of FIG. 5l taken along a cut-line 5m-5m of FIG. 5l.
Figure 5J:
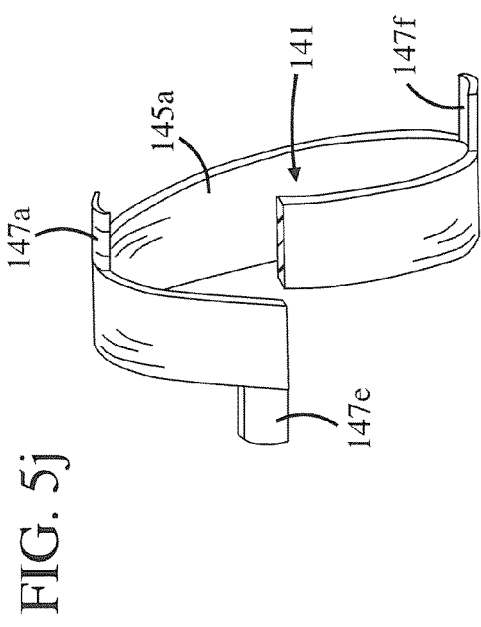
FIG. 5j is a perspective view of the helical band coil of the helical reinforcement member of FIGS. 5a, 5b and 5c having three arms connected thereto.
Figure 5L:
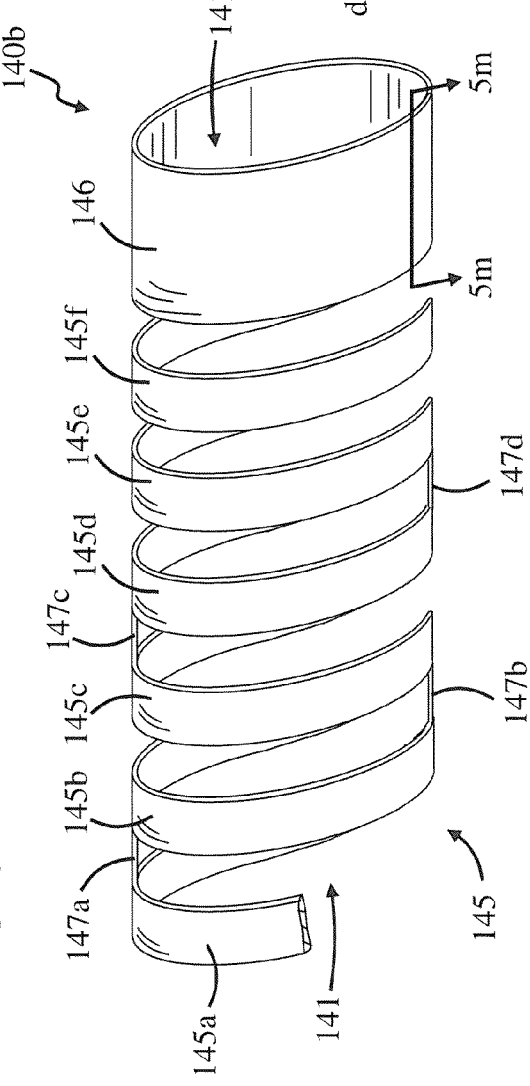
FIG. 5l is a perspective view of another embodiment of a helical reinforcement member, which can be included with the catheter of FIG. 1.

FIG. 5m is a sectional view of non-helical band coil 146 taken along a cut-line 5m-5m of FIG. 5l. In this embodiment, non-helical band coil 146 is band-shaped because its cross-sectional width, denoted as dimension $d_3$ in FIG. 5m, is greater than its cross-sectional thickness, denoted as dimension $d_2$. Non-helical band coil 146 has a different cross-sectional dimension than the other coils of reinforcement member 140b because it has a cross-sectional dimension $d_3$ that is greater than cross-sectional dimension $d_1$ (FIG. 5e) of helical band coils 145a-145f.

It should also be noted that some helical reinforcement members include some helical band coils that are restricted from stretching and compressing, and other helical band coils that are not restricted from stretching and compressing. A helical reinforcement member that includes some helical band coils that are restricted from stretching and compressing and other helical band coils that are not restricted from stretching and compressing is useful for many different reasons. For example, in some embodiments of catheter 110, the helical band coils that are not restricted from stretching and compressing extend through proximal portion 113a and the other helical coil bands that are restricted from stretching and compressing extend through distal portion 113b (FIGS. 1 and 2). In one particular embodiment, the helical band coils that are not restricted from stretching and compressing extend through nasal passage 101 and the other helical coil bands that are restricted from stretching and compressing extend through gastrointestinal tract 103 (FIGS. 1 and 2). Several examples of helical reinforcement members that include helical band coils that are restricted from stretching and compressing, and other helical band coils that are not restricted from stretching and compressing will be discussed in more detail presently.

Figure 5N:
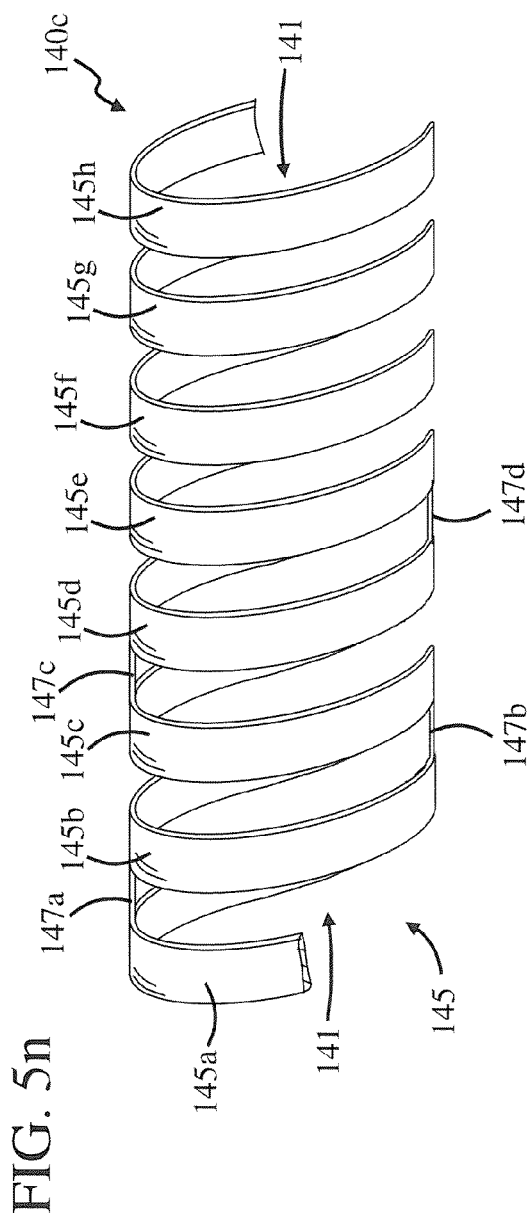
FIGS. 5n and 5o are perspective and side views, respectively, of another embodiment of a helical reinforcement member, which can be included with the catheter of FIG. 1.
Figure 5O:
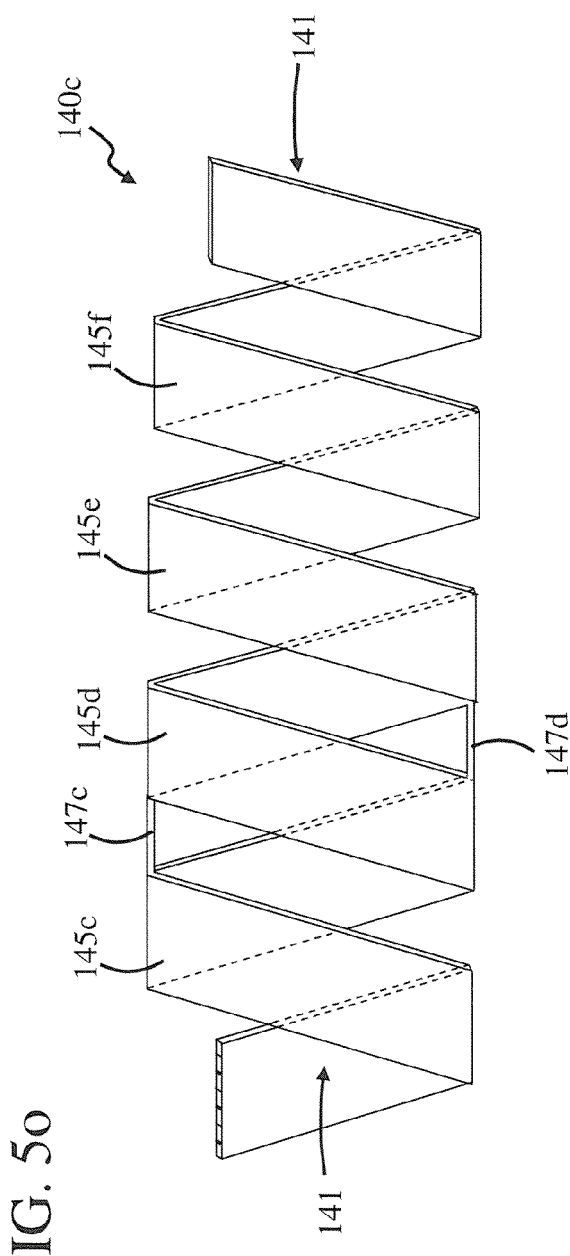

FIGS. 5n and 5o are perspective and side views, respectively, of a helical reinforcement member, denoted as helical reinforcement member 140c, which includes some helical band coils that are restricted from stretching and compressing, and other helical band coils that are not restricted from stretching and compressing. In this embodiment, helical reinforcement member 140c includes helical reinforcement member 140, which is described in more detail above. Further, helical reinforcement member 140c includes helical coil bands 145f, 145g and 145h coupled together. In particular, helical coil band 145f is coupled to helical coil band 145e, and helical coil band 145g is coupled to helical coil band 145f. Further, helical coil band 145h is coupled to helical coil band 145g. Reinforcement member channel 141 extends through helical coil bands 145a-145h.

It should be noted that helical reinforcement member 140c includes a single elongate piece of material that has a helical shape. Hence, the helical coil bands of helical reinforcement member 140c correspond to coils of the single elongate piece of material.

In this embodiment, helical coil bands 145a-145e are coupled together with arms 147a-147d, as discussed in more detail above with FIG. 5a. Helical coil bands 145a-145e are coupled together with arms 147a-147d so they are restricted from stretching and compressing, as discussed in more detail above. However, helical coil bands 145e-145h are not coupled together with arms so they are not restricted from stretching and compressing. In particular, helical coil bands 145e-145h are not coupled together with arms so they are not restricted from stretching and compressing in direction 128. Hence, helical reinforcement member 140c includes some helical band coils which are restricted from stretching and compressing, and other helical band coils which are not restricted from stretching and compressing.

FIG. 5p is a side view of a helical reinforcement member 140d. In this embodiment, helical reinforcement member 140d includes some helical band coils that are restricted from stretching and compressing, and other helical band coils that are not restricted from stretching and compressing. In this embodiment, helical reinforcement member 140c includes helical reinforcement member 140, which is described in more detail above. Further, helical reinforcement member 140c includes helical coil bands 145f, 145g and 145h coupled together. In particular, helical coil band 145f is coupled to helical coil band 145e, and helical coil band 145g is coupled to helical coil band 145f. Further, helical coil band 145h is coupled to helical coil band 145g. Reinforcement member channel 141 extends through helical coil bands 145a-145h.

It should be noted that helical reinforcement member 140c includes a single elongate piece of material that has a helical shape. Hence, the helical coil bands of helical reinforcement member 140c correspond to coils of the single elongate piece of material.

In this embodiment, helical coil bands 145a-145e are coupled together with arms 147a-147d, as discussed in more detail above with FIG. 5a. Helical coil bands 145a-145e are coupled together with arms 147a-147d so they are restricted from stretching and compressing, as discussed in more detail above. However, helical coil bands 145e-145h are not coupled together with arms so they are not restricted from stretching and compressing. In particular, helical coil bands 145e-145h are not coupled together with arms so they are not restricted from stretching and compressing in direction 128. Hence, helical reinforcement member 140c includes some helical band coils which are restricted from stretching and compressing, and other helical band coils which are not restricted from stretching and compressing.

The gastrointestinal catheter of the present may be made of a thin wall, biocompatible plastic elastomer, such as but not limited to polyurethane, reinforced with a thin helical spring band, such as but not limited to a thin helical spring band of stainless steel. The total wall thickness of, for example, a 6 mm I.D. catheter made in accordance with the present invention can be less than about $\frac{1}{30}^{th}$ its O.D. (one-half to 1 Fr unit) which is only 10-20% the wall thickness of a conventional catheter.

The reinforcing spring band may be made in two layers, as a double, overlapping helix, each band of half (or less) the minimum thickness for maintenance of structural stability by a single helical band.

The feeding catheter of the present invention may have a single lumen to intermittently deliver or aspirate. The catheter may have a second lumen to permit simultaneous feeding and aspiration of swallowed air and/or undesirable fluids. Additional channels may be present to accommodate inflation of balloons, and/or incorporation of sensors.

A fine cloth mesh sleeve, such as, but not limited to polyester, nylon, or a mixture thereof, tightly encases the otherwise exposed distal helical spring band may be utilized. The fine cloth mesh sleeve is generally about 0.002" thick. This allows free inflow of the gastric and intestinal liquids surrounding that section of the catheter and provides longitudinal stability. The impervious plastic layer will overlay the proximal portion of the spring band, with an approximately one inch of overlap to secure the cloth mesh sleeve in place. The terminal end of the sleeve can be secured to the terminal end of the spring band with adhesive or by other mechanical means.

The cloth mesh sleeve may encase the entire length of underlying helical spring band (not shown). An extremely thin layer, about 0.00025" of heat shrinkable polyester or polyolefin tubing, can be applied to overlay the proximal segment of the catheter, making it impervious to fluid. Heat shrink tubing usually imparts a relative inflexibility to the underlying material. By making this heat shrink tubing ultra-thin, adequate flexibility is achieved. However, this layer may be at risk for "cutting" by the underlying stainless steel spring band. The cloth mesh sleeve between the heat shrink tubing and spring band would protect the former while minimizing the thickness.

There is minimal adhesion between the surfaces of the reinforcing spring band, of for example stainless steel and the plastic elastomer, such as polyurethane. The band could shift within the plastic tubing as the catheter flexed, and thereby permit kinking. It has been found that the intrusion of the plastic between the coils by the force of its elastic recoil significantly limits the movement of the coils and reduces kinking. The catheter is assembled so that the elastomer exerts constant tension on the helical spring band.

Thin walled tubing having a wall thickness of less than about 0.003" and whose undistended I.D. is significantly less than the O.D. of the reinforcing spiral band is used. A vacuum process is used to distend the undersized elastomeric tubing, insert the proximal segment of the spring band, and release the vacuum. The recoil of the elastomer will force it into the spaces between the coils, keeping them separated, as well as mechanically holding the coils in place with continuous tension.

The proximal segment of the aspiration catheter will have an outer covering of impervious elastomer. The distal segment of the spring band is covered with a "filter sleeve" of very thin, less than about 0.002", knitted plastic mesh (e.g., polyester). The elastomer will overlap the sleeve and secure it in place. This distal catheter segment will be positioned to lie within the stomach and intestine to aspirate these sites.

A small bore feeding tube may be passed co-axially down the aspiration catheter to extend a short distance, less than about 6 cm beyond, but still within the same anatomical segment of intestine, (more distal duodenum or more distal jejunum). The feeding and aspiration sites of the present invention are in the same intestinal segment. The double helix allows for the automatic formation of aspiration orifices. The double helix has multiple trapezoidal openings where the gaps overlap. By simply leave the end segment uncovered by the elastomer, aspiration orifices are formed.

The feeding device of the present invention with an internal diameter of about 6 mm will have an O.D. of less than about 20 Fr units, wherein 3 Fr units=1 mm.

Figure 5Q:
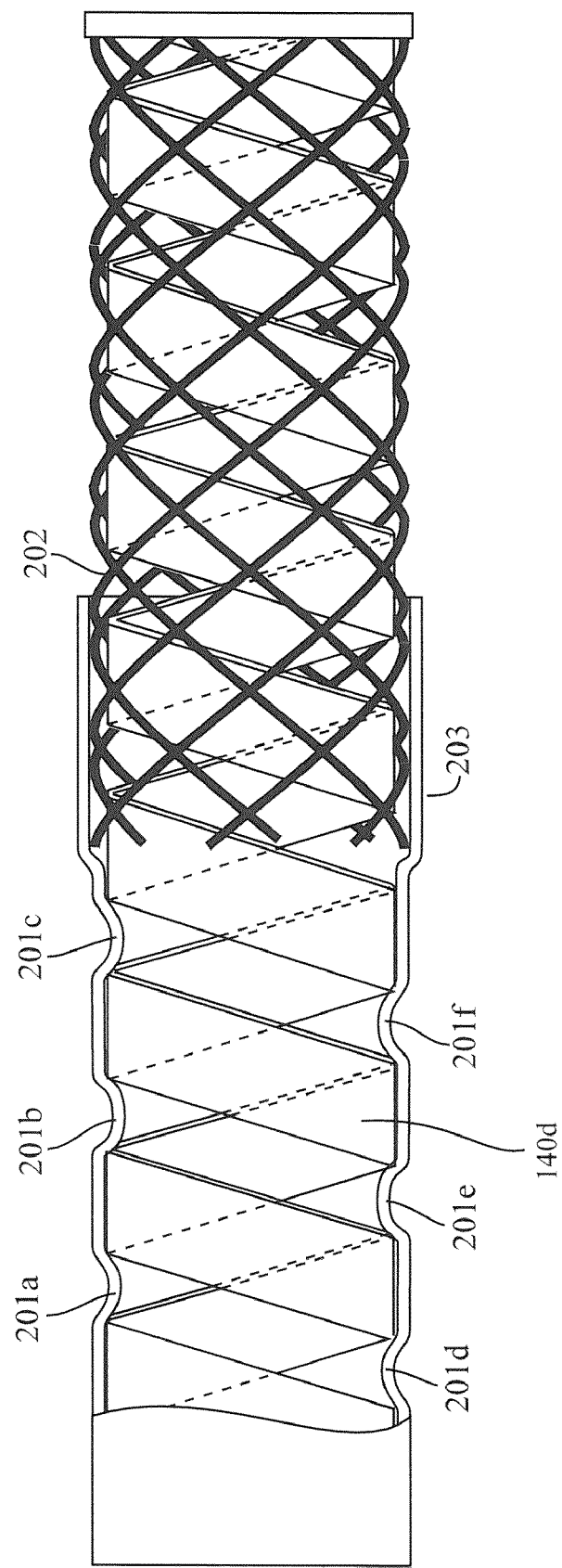
FIG. 5q is a perspective view of another embodiment of a helical reinforcement member, which can be included with the catheter of FIG. 1.

FIG. 5q is a perspective view of helical reinforcement member 140d with a cutaway of a portion of the elastomer. The elastomer 201a, b, c, d, e, f is covering (dipping down between bands), a fine mesh sleeve 202 (with holes larger than the spacing between coils) is covering the band on the right, with an elastomer short zone of overlap 203, the coils covered by mesh overlaid with elastomer.

The reinforcing spring band may be made in two layers, as a double, overlapping helix, each band of half (or less) the minimum thickness for maintenance of structural stability by a single helical band. The impervious elastomer sheath will cover only the proximal portion of the aspiration catheter. The distal portion of the "double helix," within the stomach and intestine, will be bare. The right hand spiral over the left hand spiral coils will maintain their positions, much like layers of plywood. However, the spaces between adjacent coils ($d_{gap}$) of the overlying layer overlapping the spaces ($d_{gap}$) between the underlying layer serve as a large number of aspiration orifices within the stomach and intestine.

FIGS. 6a and 6b are perspective and end views, respectively, of a non-helical reinforcement member 150. As discussed in more detail below, non-helical reinforcement member 150 is allowed to bend in directions 126 and 127, and is restricted from stretching and compressing in direction 128 (FIGS. 6a and 6b). Non-helical reinforcement member 150 has an outer dimension, which is denoted as dimension $d_{Coil}$ in FIG. 6b. In this embodiment, outer dimension $d_{Coil}$ corresponds to the outer diameter of non-helical reinforcement member 150.

As shown in FIG. 6b, non-helical reinforcement member 150 has reinforcement member channel 141 extending therethrough, and outer reinforcement member surface 142b and inner reinforcement member surface 143b. Inner reinforcement member surface 143b faces reinforcement member channel 141 and outer reinforcement member surface 142b faces away from reinforcement member channel 141. It should be noted that outer reinforcement member surface 142b and inner reinforcement member surface 143b are annular surfaces which extend around reinforcement member channel 141. Further, outer reinforcement member surface 142b and inner reinforcement member surface 143b are curved surfaces which curve around reinforcement member channel 141. Outer reinforcement member surface 142b and inner reinforcement member surface 143b are non-helical surfaces because they do not extend helically around reinforcement member channel 141.

In this embodiment, non-helical reinforcement member 150 includes a number of non-helical band coils 155a, 155b, 155c, 155d and 155e, wherein helical band coil 155a is shown in a perspective view in FIG. 6c. Non-helical band coils 155a, 155b, 155c, 155d and 155e are coupled together so reinforcement member 150 has a non-helical shape. It should be noted that reinforcement member channel 141 extends through non-helical band coils 155a, 155b, 155c, 155d and 155e. It should also be noted that the outer diameter of non-helical band coils 155a, 155b, 155c, 155d and 155e correspond to dimension $d_{Coil}$.

In this embodiment, non-helical band coils 155a, 155b, 155c, 155d and 155e each include a single elongate piece of material which has a ring shape. Hence, the band coils of non-helical reinforcement member 150 correspond to separate ring shaped bands of material.

In this embodiment, non-helical reinforcement member 150 includes arms 147a, 147b, 147c and 147d, which restrict the ability of non-helical reinforcement member 150 to stretch and compress in direction 128, and allow non-helical reinforcement member 150 to bend in directions 126 and 127. Arm 147a is connected between upper portions of non-helical band coils 155a and 155b and arm 147b is connected between lower portions of helical band coils 155b and 155c. Arm 147c is connected between upper portions of helical band coils 155c and 155d, and arm 147d is connected between lower portions of helical band coils 155d and 155e.

FIG. 6d is a sectional view of helical reinforcement member 150 taken along a cut-line 6d-6d of FIG. 6a. In particular, FIG. 6d is a sectional view of non-helical band coil 155e taken along cut-line 6d-6d of FIG. 6a. In this embodiment, non-helical band coil 155e is band-shaped because its cross-sectional width, denoted as dimension $d_1$ in FIG. 6d, is greater than its cross-sectional thickness, denoted as dimension $d_2$. Non-helical band coil 155e does not have a circular cross-sectional shape as does helical spring 130, as shown in FIG. 4d. It should be noted that non-helical band coils 155a, 155b, 155c and 155d also have cross-sectional dimensions $d_1$ and $d_2$.

It should also be noted that upper and lower portions of some of the non-helical band coils of helical reinforcement member 140 are not coupled together with arms so that there is a gap therebetween. For example, as shown in FIG. 6a, gap 149a extends between the lower portion of non-helical band coils 155a and 155b, and gap 149b extends between the upper portion of non-helical band coils 155b and 155c. Further, gap 149c extends between the lower portion of non-helical band coils 155c and 155d, and gap 149d extends between the upper portion of non-helical band coils 155d and 155e. It should be noted that, in this embodiment, gaps 149a, 149b, 149c and 149d extend annularly around channel 141. Further, gaps 149a, 149b, 149c and 149d extend non-helically around channel 141. Gaps 149a, 149b, 149c and 149d extend non-helically around channel 141 because band coils 155a, 155b, 155c, 155d and 155e are non-helical band coils. In this way, gaps 149a, 149b, 149c and 149d are non-helical gaps.

Figure 6E:
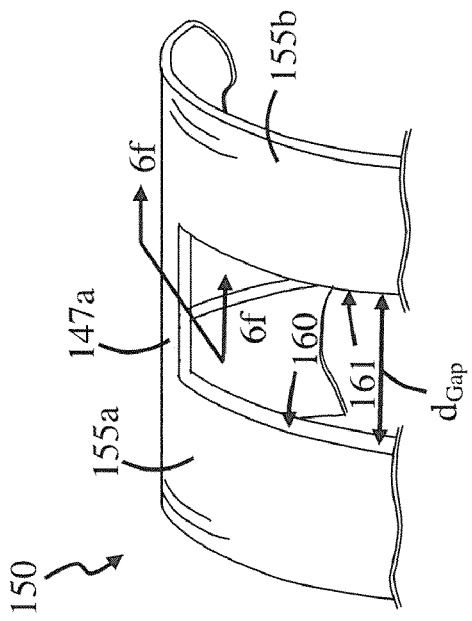
FIG. 6e is a close-up perspective view of the helical reinforcement member of FIGS. 6a and 6b.
Figure 6F:
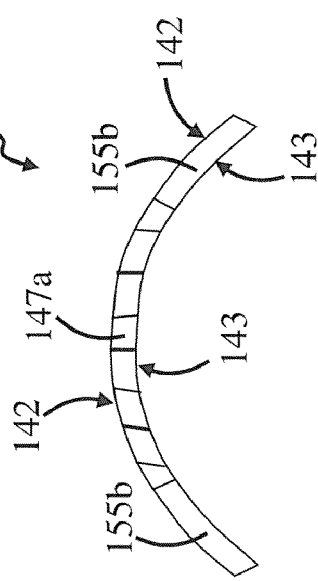
FIG. 6f is a cut-away side view of the helical reinforcement member of FIGS. 6a and 6b taken along a cut-line 6f-6f of FIG. 6e.
Figure 6G:
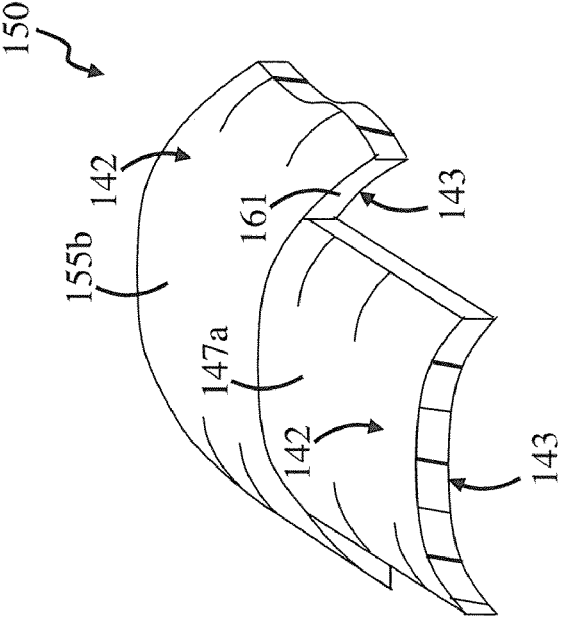
FIG. 6g is a perspective view of the helical reinforcement member of FIGS. 6a and 6b taken along cut-line 6f-6f of FIG. 6e.

FIG. 6e is a perspective view of non-helical reinforcement member 150 in a region 154 of FIG. 6a. FIG. 6f is a cut-away side view of non-helical reinforcement member 150 in region 154 taken along a cut-line 6f-6f of FIG. 6e. FIG. 6g is a perspective view of non-helical reinforcement member 150 in region 154 taken along cut-line 6f-6f of FIG. 6e.

Arm 147a extends between, and is coupled to, non-helical band coils 155a and 155b. In this way, non-helical reinforcement member 150 includes non-helical band coils coupled together with an arm. Arm 147a restricts the ability of non-helical band coils 155a and 155b to move towards each other. Hence, arm 147a restricts the ability of non-helical band coils 155a and 155b to be compressed. Arm 147a restricts the ability of non-helical band coils 155a and 155b to move away from each other. Hence, arm 147a restricts the ability of non-helical band coils 155a and 155b to be stretched. In this way, non-helical reinforcement member 150 includes an arm which restricts the ability of the non-helical band coils of non-helical reinforcement member 150 to be stretched and compressed.

Non-helical band coils 155a and 155b include edges 160 and 161, respectively, which extend along them. In this embodiment, arm 147a extends between edges 160 and 161. In this way, non-helical reinforcement member 150 includes an arm which extends between edges of non-helical band coils. Arm 147a restricts the ability of edges 160 and 161 to move towards each other. Hence, arm 147a restricts the ability of non-helical band coils 155a and 155b to be compressed. Arm 147a restricts the ability of edges 160 and 161 to move away from each other. Hence, arm 147a restricts the ability of non-helical band coils 155a and 155b to be stretched. In this way, non-helical reinforcement member 150 includes an arm which restricts the ability of edges of non-helical band coils of non-helical reinforcement member 150 to move towards and away from each other.

In this embodiment, edges 160 and 161 are opposed to each other, and arm 147a extends between them. In this way, non-helical reinforcement member 150 includes an arm which extends between opposed edges of non-helical band coils. Arm 147a restricts the ability of opposed edges 160 and 161 to move towards each other. Hence, arm 147a restricts the ability of non-helical band coils 155a and 155b to be compressed. Arm 147a restricts the ability of opposed edges 160 and 161 to move away from each other. Hence, arm 147a restricts the ability of non-helical band coils 155a and 155b to be stretched. In this way, non-helical reinforcement member 150 includes an arm which restricts the ability of opposed edges of non-helical band coils of non-helical reinforcement member 150 to be moved towards and away from each other.

Non-helical band coils 155a and 155b are adjacent to each other because they are adjacent coils. Hence, non-helical reinforcement member 150 includes an arm connected between adjacent non-helical band coils. Arm 147a restricts the ability of adjacent non-helical band coils 155a and 155b to move towards each other. Hence, arm 147a restricts the ability of adjacent non-helical band coils 155a and 155b to be compressed. Arm 147a restricts the ability of adjacent non-helical band coils 155a and 155b to move away from each other. Hence, arm 147a restricts the ability of adjacent non-helical band coils 155a and 155b to be stretched. In this way, non-helical reinforcement member 150 includes an arm which restricts the ability of adjacent non-helical band coils of non-helical reinforcement member 150 to be stretched and compressed.

It should be noted that, in this embodiment, arm 147b extends between opposed edges 160 and 161 of non-helical band coils 155a and 155b. Hence, arm 147b restricts the ability of edges 160 and 161 to move towards each other. In this way, arm 147b restricts the ability of non-helical band coils 155a and 155b to be compressed. Arm 147b restricts the ability of edges 160 and 161 to move away from each other. In this way, arm 147b restricts the ability of non-helical band coils 155a and 155b to be stretched. Hence, non-helical reinforcement member 150 includes more than one arm which restricts the ability of adjacent non-helical band coils of non-helical reinforcement member 150 to move towards and away from each other.

Arms 147c and 147d extend between opposed edges of non-helical band coils 155c and 155d. Hence, arms 147c and 147d restrict the ability of non-helical band coils 155c and 155d to move towards each other. In this way, arms 147c and 147d restrict the ability of non-helical band coils 155c and 155d to be compressed. Arms 147c and 147d restrict the ability of edges 160 and 161 to move away from each other. In this way, arms 147b, 147c and 147d restrict the ability of non-helical band coils 155c and 155d to be stretched.

It should be noted that non-helical reinforcement member 150 stretches in response to one or more of its non-helical band coils stretching. Hence, arms 147a, 147b, 147c and 147d restrict the ability of non-helical reinforcement member 150 to stretch because they restrict the ability of the non-helical band coils of non-helical reinforcement member 150 to stretch. Hence, non-helical reinforcement member 150 includes an arm which restricts it from stretching.

Further, non-helical reinforcement member 150 compresses in response to one or more of its non-helical band coils compressing. Hence, arms 147a, 147b, 147c and 147d restrict the ability of non-helical reinforcement member 150 to compress because they restrict the ability of the non-helical band coils of non-helical reinforcement member 150 to compress. Hence, non-helical reinforcement member 150 includes an arm which restricts it from compressing. In this way, non-helical reinforcement member 150 includes an arm which restricts the ability of the non-helical band coils of non-helical reinforcement member 150 to stretch and compress.

It should be noted that, in some embodiments, non-helical reinforcement member 150 includes some non-helical band coils which are coupled to adjacent non-helical band coils through one or more arms. For example, FIG. 6h is a perspective view of non-helical band coil 155a. In this embodiment, arms 147a, 147e and 147f extend outwardly from edges of non-helical band coil 155a, and are coupled to adjacent non-helical band coils, which are not shown for simplicity.

Figure 6I:
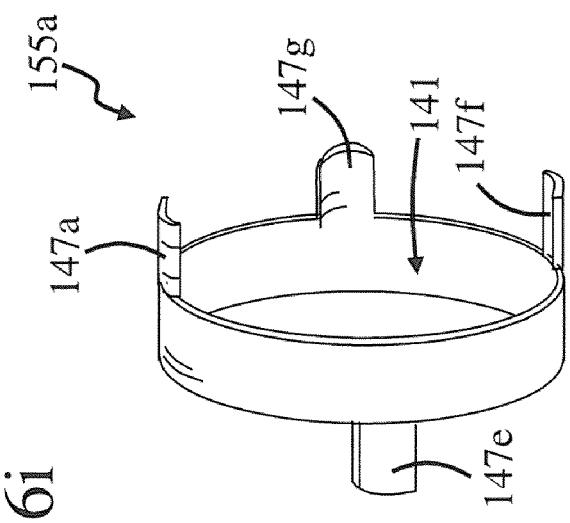
FIG. 6i is a perspective view of the helical band coil of the non-helical reinforcement member of FIGS. 6a and 6b having four arms connected thereto.
Figure 6H:
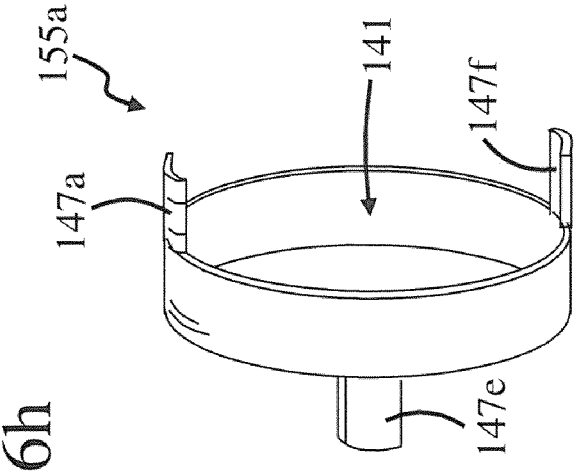
FIG. 6h is a perspective view of the non-helical band coil of the helical reinforcement member of FIGS. 6a and 6b having three arms connected thereto.

FIG. 6i is a perspective view of non-helical band coil 155a. In this embodiment, arms 147a, 147e, 147f and 147g extend outwardly from edges of non-helical band coil 155a, and are coupled to adjacent non-helical band coils, which are not shown for simplicity.

Figure 6J:
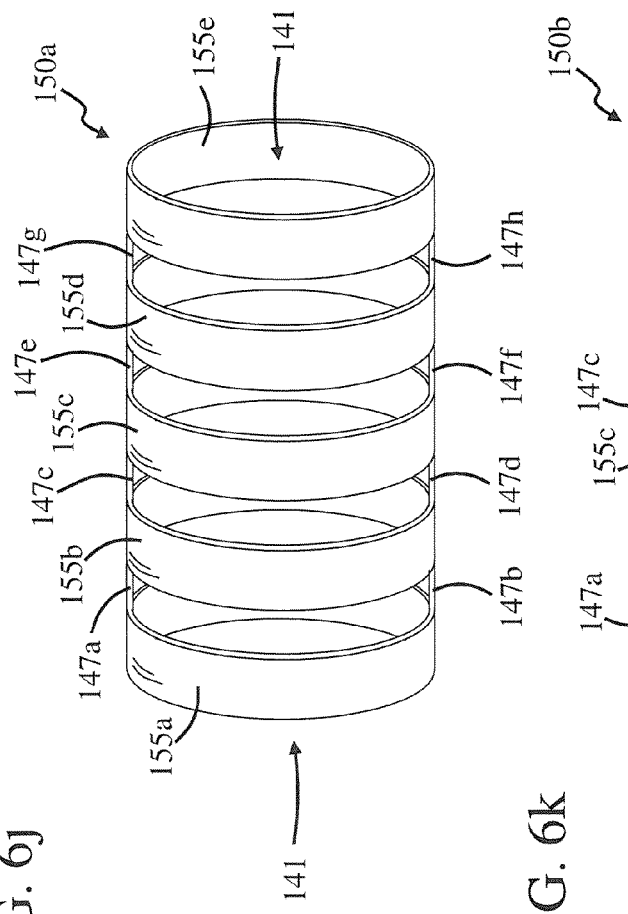
FIG. 6j is a perspective view of another embodiment of a non-helical band coil, which can be included with the catheter of FIG. 1.

An example of a non-helical reinforcement member, denoted as non-helical reinforcement member 150a, which includes arms extending between upper and lower edges of each non-helical band coils is shown in FIG. 6j. In general, a non-helical reinforcement member is allowed to bend more as the number of gaps extending between the upper and lower edges of the non-helical band coils increases. A non-helical reinforcement member is allowed to bend less as the number of arms extending between the upper and lower edges of the non-helical band coils increases. Further, a non-helical reinforcement member is allowed to bend less as the number of gaps extending between the upper and lower edges of the non-helical band coils decreases. A non-helical reinforcement member is allowed to bend more as the number of arms extending between the upper and lower edges of the non-helical band coils decreases.

Figure 6K:
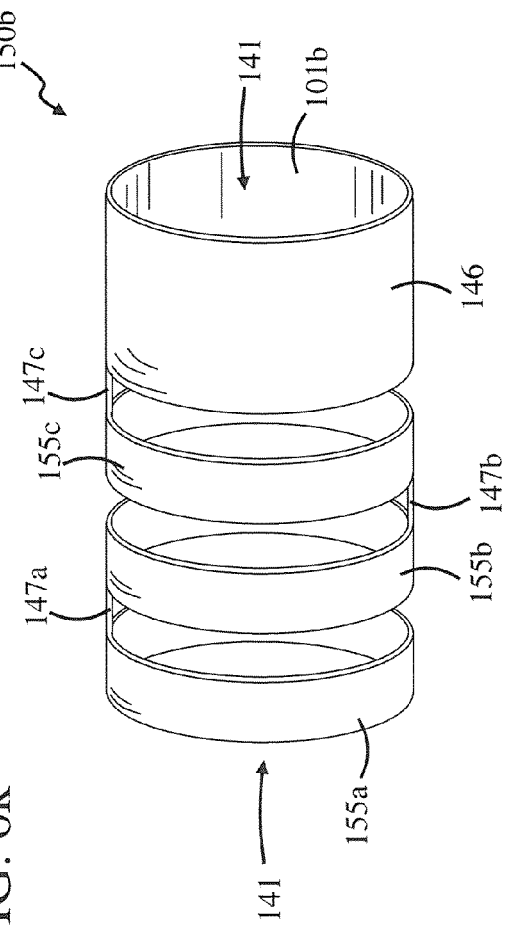
FIG. 6k is a perspective view of another embodiment of a non-helical reinforcement member, which can be included with the catheter of FIG. 1.

It should be noted that some reinforcement members include non-helical band coils that have the same or a different cross-sectional dimension $d_1$ than the other non-helical coils of the non-helical reinforcement member. For example, FIG. 6k is a perspective view of a non-helical reinforcement member, denoted as non-helical reinforcement member 150b, which includes non-helical band coil 155a, 155b and 155c connected together as shown in FIG. 6a. In this embodiment, non-helical reinforcement member 150b includes non-helical band coil 146 coupled to helical band coil 155c through arm 147c. Non-helical band coil 146 is non-helical because it is ring shaped and not helical shaped, as in non-helical band coils 155a-155e. More information regarding reinforcement members which include non-helical band coils is provided above with the discussion of FIGS. 5a-5p. As discussed in more detail above, FIG. 5m is a sectional view of non-helical band coil 146 taken along a cut-line 5m-5m of FIG. 5m.

FIGS. 7a and 7b are perspective and end views, respectively, of a resilient reinforcement member tube 151 with reinforcement member channel 141 extending therethrough. Resilient reinforcement member tube 151 is used to manufacture a helical reinforcement member or non-helical reinforcement member, as will be discussed in more detail below. Resilient reinforcement member tube 151 can include many different types of resilient material, such as materially typically included with a spring. The material of reinforcement member tube 151 is harder than the material of resilient tube 120.

The reinforcement member is manufactured from resilient reinforcement member tube 151 by removing portions of resilient reinforcement member tube 151 to form coils, arms and gaps, which are discussed in more detail above. The portions of resilient reinforcement member tube 151 can be removed in many different ways, such as by using a laser. In one embodiment, the laser is turned on and its beam is directed at outer reinforcement member surface 142 and moved across outer reinforcement member surface 142 to form the gaps of the reinforcement member. The laser is turned off and moved relative to outer reinforcement member surface 142 to form the arms and coils. It should be noted that dimension $d_{Gap}$ (FIGS. 5b, 5g, 6a and 6e) corresponds to a width of the laser beam.

FIG. 7c is a perspective view of resilient reinforcement member tube 151 showing helical reinforcement member 140 in phantom. Gaps 149a and 149b, as well as the other gaps of helical reinforcement member 140 are formed by removing portions of resilient reinforcement member tube 151. Some portions of resilient reinforcement member tube 151 that are not removed form arms 147a and 147c, as well as the other arms of helical reinforcement member 140. Other portions of resilient reinforcement member tube 151 that are not removed form helical coils 145a, 145b, 145c and 145d, as well as the other helical coils of helical reinforcement member 140. As mentioned above, a laser can be used to remove desired portions of resilient reinforcement member tube 151 to form helical reinforcement member 140.

FIG. 7d is a perspective view of resilient reinforcement member tube 151 showing non-helical reinforcement member 150 in phantom. Gaps 149a, 149b and 149c, as well as the other gaps of non-helical reinforcement member 150 are formed by removing portions of resilient reinforcement member tube 151. Some portions of resilient reinforcement member tube 151 that are not removed form arms 147a and 147c, as well as the other arms of non-helical reinforcement member 150. Other portions of resilient reinforcement member tube 151 that are not removed form non-helical coils 155b, 155c and 155d, as well as the other non-helical coils of non-helical reinforcement member 150. As mentioned above, a laser can be used to remove desired portions of resilient reinforcement member tube 151 to form non-helical reinforcement member 150.

It should be noted that the arms of the reinforcement member manufactured from resilient reinforcement member tube 151 have the same curvature of resilient reinforcement member tube 151. The curvature of resilient reinforcement member tube 151 corresponds to the curvature of outer reinforcement member surface 142 and inner reinforcement member surface 143.

It should also be noted that the coils of the reinforcement member manufactured from resilient reinforcement member tube 151 have the same curvature of resilient reinforcement member tube 151. The curvature of resilient reinforcement member tube 151 corresponds to the curvature of outer reinforcement member surface 142 and inner reinforcement member surface 143.

Figure 8A:
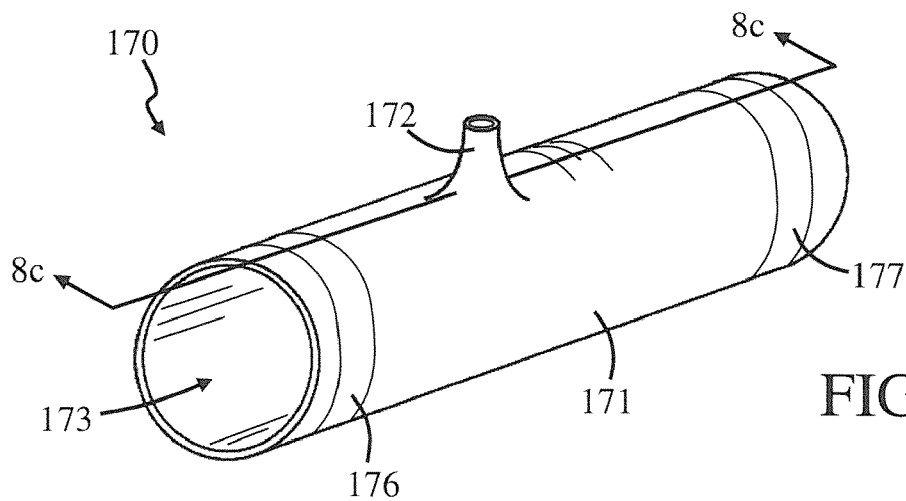
FIGS. 8a and 8b are perspective and end views, respectively, of a vacuum tube system, which is used to manufacture a catheter which includes a resilient tube and reinforcement member.
Figure 8B:
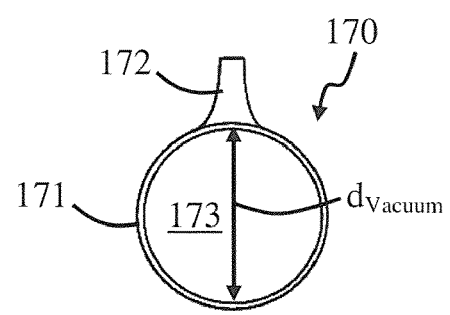
Figure 8C:
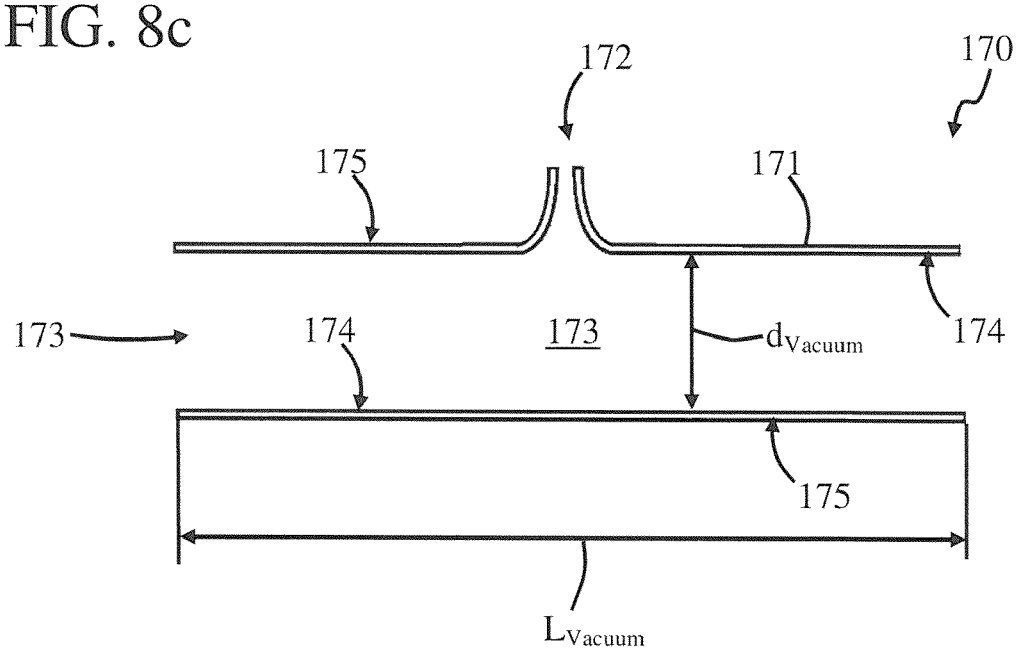

FIGS. 8a and 8b are perspective and end views, respectively, of a vacuum tube system 170, which is used to manufacture a catheter which includes a resilient tube and reinforcement member. FIG. 8c is a cut-away side view of vacuum tube system 170 taken along a cut-line 8c-8c of FIG. 8a.

In this embodiment, vacuum tube system 170 includes a vacuum tube 171 with a vacuum tube channel 173 extending therethrough. Vacuum tube 171 includes a vacuum tube inner surface 174 and vacuum tube outer surface 175, wherein vacuum tube inner surface 174 faces vacuum tube channel 173 and vacuum tube outer surface 175 faces away from vacuum tube channel 173.

Vacuum tube system 170 includes a vacuum tube nozzle 172 in fluid communication with vacuum tube channel 173 through vacuum tube 171. Vacuum tube system 170 includes vacuum tube clamps 176 and 177, which extend around the outer periphery of vacuum tube 171.

Vacuum tube 171 has a length $L_{Vacuum}$, as indicated in FIG. 8c. Length $L_{Vacuum}$ can have many different values. In one embodiment, length $L_{Vacuum}$ has a value that is about equal to the length of catheter 110 (FIG. 2). As mentioned above, the length of catheter 110 corresponds to the sum of lengths $L_1$ and $L_2$. In one embodiment, length $L_{Vacuum}$ is between about thirty inches to about sixty inches. In another embodiment, length $L_{Vacuum}$ is between about thirty five inches to about forty five inches.

Vacuum tube 171 has a dimension $d_{Vacuum}$, as indicated in FIG. 8c. Dimension $d_{Vacuum}$ corresponds to an inner dimension of vacuum tube channel 173. The inner dimension of vacuum tube channel 173 corresponds to a diameter of vacuum tube channel 173 because vacuum tube 171 is circular in shape, as shown in FIG. 8b.

Dimension $d_{Vacuum}$ can have many different values. In one embodiment, dimension $d_{Vacuum}$ has a value in a range between about 0.100 inches to about 0.500 inches. In other embodiments, dimension $d_{Vacuum}$ has a value in a range between about 0.200 inches to about 0.500 inches.

Figure 9A:
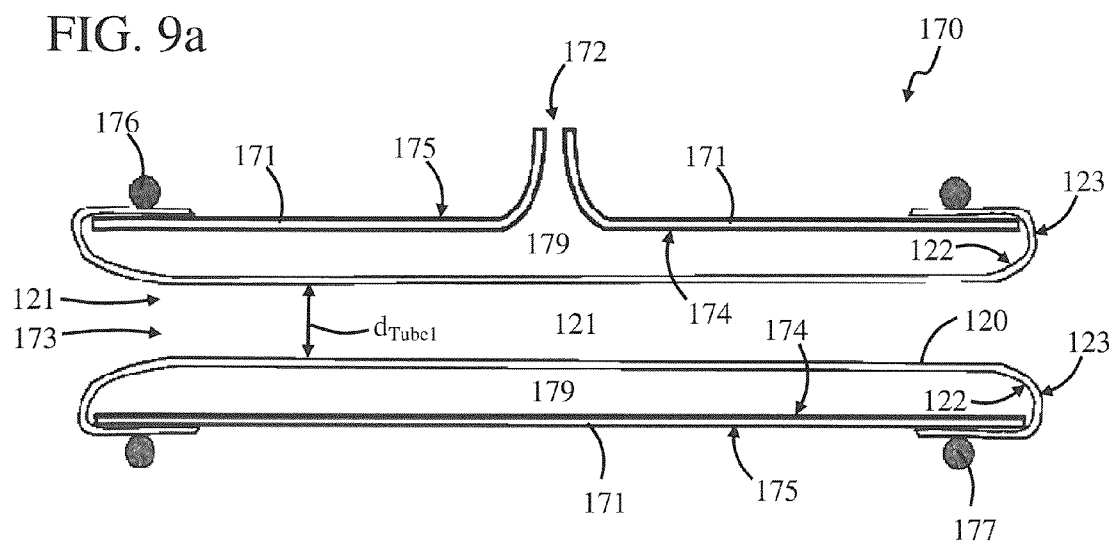
FIGS. 9a and 9b are cut-away side views of the vacuum tube system of FIGS. 8a and 8b taken along cut-line 8c-8c, wherein the resilient tube of FIGS. 3a and 3b extends through the vacuum tube channel.

FIG. 9a is a cut-away side view of vacuum tube system 170 taken along cut-line 8c-8c, wherein resilient tube 120 extends through vacuum tube channel 173. Resilient tube 120 extends through vacuum tube channel 173 so that outer resilient tube surface 122 faces vacuum tube inner surface 174. Resilient tube 120 extends through vacuum tube channel 173 so that a vacuum region 179 is formed between resilient tube 120 and vacuum tube 171. In particular, resilient tube 120 extends through vacuum tube channel 173 so that a vacuum region 179 is formed between outer resilient tube surface 122 and vacuum tube inner surface 174. It should be noted that vacuum region 179 is in fluid communication with vacuum tube nozzle 172. Further, it should be noted that vacuum region 179 extends annularly around resilient tube 120.

Opposed ends of resilient tube 120 are folded over opposed openings of vacuum tube 171. Opposed ends of resilient tube 120 are folded over opposed openings of vacuum tube 171 so that outer resilient tube surface 122 engages vacuum tube outer surface 175. Opposed ends of resilient tube 120 are folded over opposed openings of vacuum tube 171 so that vacuum region 179 is formed between outer resilient tube surface 122 and vacuum tube inner surface 174.

Clamps 176 and 177 are positioned proximate to the opposed openings of vacuum tube 171. Clamps 176 and 177 clamp the portions of resilient tube 120 that are folded over opposed openings of vacuum tube 171 so that a seal is formed in response. The seal is formed between resilient tube 120 and vacuum tube 171, and restricts the flow of the atmosphere of vacuum region 179 therebetween.

Figure 9B:
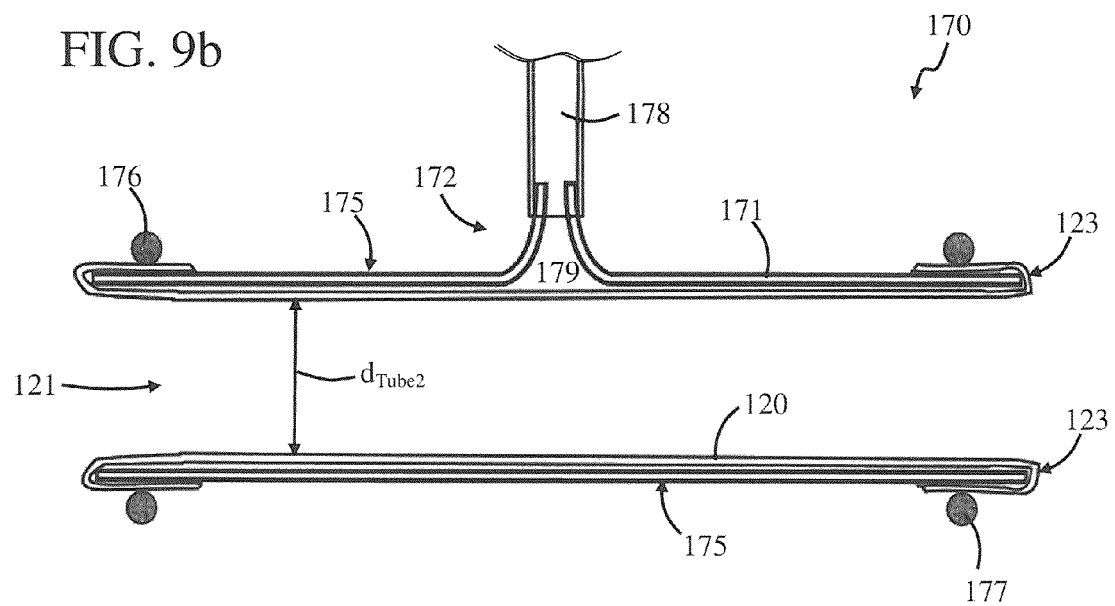

In FIG. 9b, a vacuum system hose 178 is connected to vacuum tube nozzle 172 so that vacuum system hose 178 is in fluid communication with vacuum region 179. Vacuum system hose 178 is connected to a vacuum system (not shown), which is capable of adjusting the pressure of the atmosphere of vacuum region 179. The vacuum system is capable of increasing and decreasing the pressure of the atmosphere of vacuum region 179.

Resilient tube 120 moves towards vacuum tube 171 in response to reducing the pressure of the atmosphere of vacuum region 179. In particular, outer resilient tube surface 122 moves towards vacuum tube inner surface 174 in response to reducing the atmosphere of vacuum region 179. Outer resilient tube surface 122 moves towards vacuum tube inner surface 174 because force $F_1$ decreases and force $F_2$ increases (FIG. 3b) in response to reducing the pressure of the atmosphere of vacuum region 179. It should be noted that dimension $d_{Tube}$ (FIG. 3b) increases in response to reducing the atmosphere of vacuum region 179. It is desirable to increase dimension $d_{Tube}$ when it is desirable to extend a reinforcement member through resilient tube channel 121.

Further, resilient tube 120 moves away from vacuum tube 171 in response to increasing the atmosphere of vacuum region 179. In particular, outer resilient tube surface 122 moves away from vacuum tube inner surface 174 in response to increasing the atmosphere of vacuum region 179. Outer resilient tube surface 122 moves away from vacuum tube inner surface 174 because force $F_1$ increases and force $F_2$ decreases (FIG. 3b) in response to increasing the pressure of the atmosphere of vacuum region 179. It should be noted that dimension $d_{Tube}$ (FIG. 3b) decreases in response to increasing the atmosphere of vacuum region 179. It is desirable to decrease dimension $d_{Tube}$ when it is desirable to stretch resilient tube 120 over a reinforcement member extending through resilient tube channel 121.

Figure 9C:
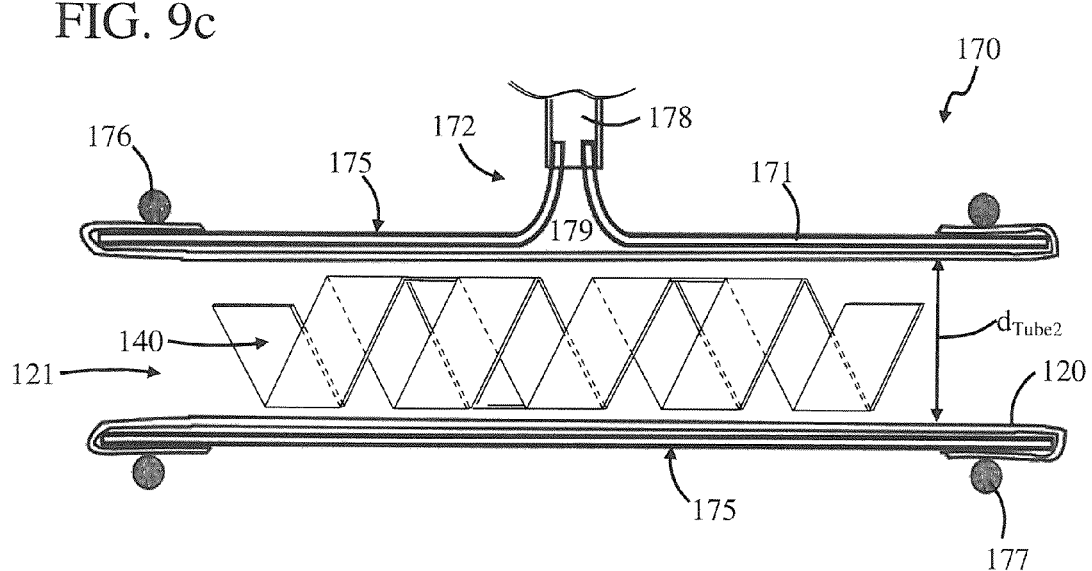
FIG. 9c is a cut-away side view of the vacuum tube system of FIGS. 8a and 8b and the resilient tube of FIGS. 3a and 3b.

FIG. 9c is a cut-away side view of vacuum tube system 170 and resilient tube 120, as shown in FIG. 9b. In FIG. 9c, reinforcement member 140 extends through resilient tube 120. In particular, reinforcement member 140 extends through resilient tube channel 121. As mentioned above, reinforcement member 140 has dimension $d_{coil}$, which corresponds to its outer diameter. Dimension $d_{Tube}$ is increased so that it is greater than dimension $d_{coil}$. Dimension $d_{Tube}$ is increased so that it is greater than dimension $d_{coil}$ so that reinforcement member 140 can extend through resilient tube channel 121. Dimension $d_{Tube}$ is increased in response to reducing the pressure of the atmosphere of vacuum region 179. As mentioned above, force $F_1$ is decreased and force $F_2$ is increased in response to increasing the pressure of the atmosphere of vacuum region 179.

Figure 9D:
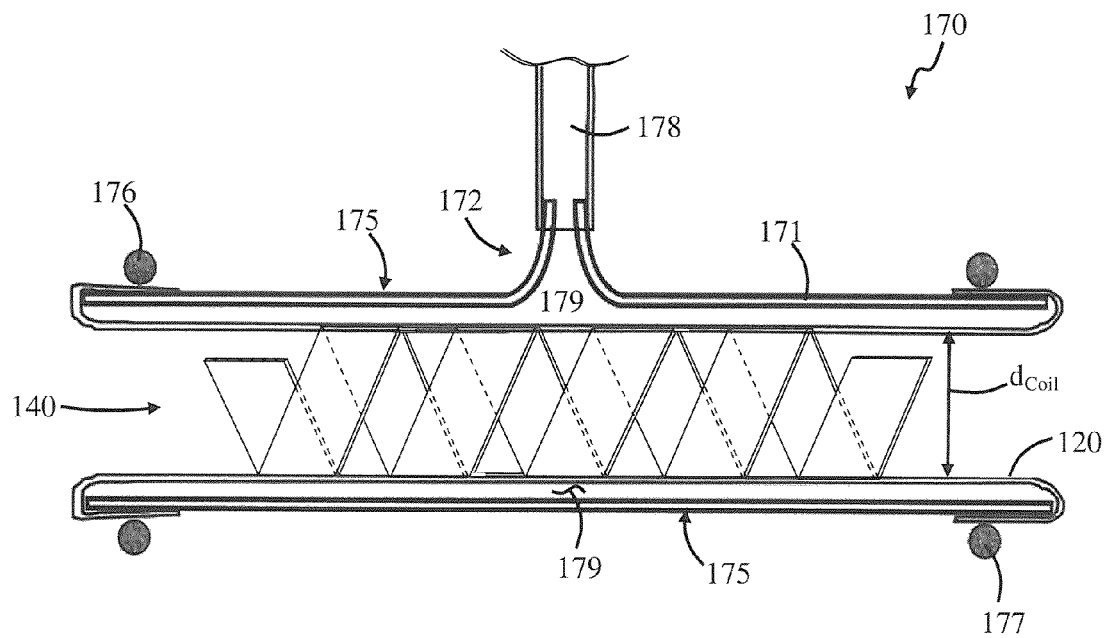
FIG. 9d is a cut-away side view of the vacuum tube system of FIGS. 8a and 8b, resilient tube FIGS. 3a and 3b and reinforcement member of FIGS. 5a, 5b and 5c.

FIG. 9d is a cut-away side view of vacuum tube system 170, resilient tube 120 and reinforcement member 140, as shown in FIG. 9c. In FIG. 9d, reinforcement member 140 extends through resilient tube 120, and the pressure of the atmosphere of vacuum region 179 is increased so that resilient tube 120 engages reinforcement member 140. Dimension $d_{Tube}$ is decreased so that it is driven to dimension $d_{Coil}$. Dimension $d_{Tube}$ is decreased in response to reducing the pressure of the atmosphere of vacuum region 179. As mentioned above, force $F_1$ is increased and force $F_2$ is decreased in response to decreasing the pressure of the atmosphere of vacuum region 179.

The pressure of the atmosphere of vacuum region 179 is increased so that resilient tube 120 engages reinforcement member 140 in response. In particular, the pressure of the atmosphere of vacuum region 179 is increased so that inner resilient tube surface 123 engages helical reinforcement member 140. Resilient tube 120 engages reinforcement member 140 so that inner resilient tube surface 123 engages the helical band coils, which are discussed in more detail above. In this way, catheter 110a is manufactured, wherein catheter 110a includes resilient tube 120 and helical reinforcement member 140. Catheter 110a will be discussed in more detail with FIGS. 10a, 10b and 10c.

It should be noted that helical reinforcement member 140 of FIG. 9c can be replaced with another reinforcement member, such as helical spring 130 and non-helical reinforcement member 150. In this way, a catheter 110b, which includes resilient tube 120 and non-helical reinforcement member 150, is manufactured. Catheter 110b will be discussed in more detail with FIGS. 11a, 11b and 11c.

FIGS. 10a and 10b are perspective and end views, respectively, of catheter 110a, wherein helical reinforcement member 140 is shown as partially extending through resilient tube 120. FIG. 10c is a close-up view of catheter 110a in a region 117 of FIG. 10a.

Resilient tube 120 is corrugated in response to engaging helical reinforcement member 140. In particular, portions of resilient tube 120 proximate to the gaps of helical reinforcement member 140 extend inwardly to form a corrugation. For example, the portion of resilient tube 120 proximate to helical gap 148a forms a helical corrugation 152. It should be noted that corrugation 152 is a helical corrugation because, as discussed in more detail above with FIGS. 5a-5n, helical reinforcement member 140 includes helical band coils adjacent to helical gap 148a. In particular, corrugation 152 is a helical corrugation because helical reinforcement member 140 includes helical band coils adjacent to helical gap 148a.

It should be noted that, in some embodiments, resilient tube 120 and helical reinforcement member 140 operate as an aspiration tube. In some of these embodiments, a feeding tube (not shown) extends through resilient tube channel 121 and reinforcement member channel 141 of member 140 so that catheter 110a operates as a dual lumen catheter.

FIGS. 11a and 11b are perspective and end views, respectively, of catheter 110b, wherein non-helical reinforcement member 150 is shown as partially extending through resilient tube 120. FIG. 11c is a close-up view of catheter 110b in a region 118 of FIG. 11a.

Resilient tube 120 is corrugated in response to engaging non-helical reinforcement member 150. In particular, portions of resilient tube 120 proximate to the gaps of non-helical reinforcement member 150 extend inwardly to form a corrugation. For example, the portion of resilient tube 120 proximate to non-helical gap 149b forms a non-helical corrugation 153. It should be noted that corrugation 153 is a non-helical corrugation because, as discussed in more detail above with FIGS. 6a-6k, non-helical reinforcement member 150 includes non-helical band coils adjacent to non-helical gap 149b. In particular, corrugation 153 is a non-helical corrugation because non-helical reinforcement member 150 includes non-helical band coils adjacent to non-helical gap 149b.

It should be noted that, in some embodiments, resilient tube 120 and non-helical reinforcement member 150 operate as an aspiration tube. In some of these embodiments, a feeding tube (not shown) extends through resilient tube channel 121 and reinforcement member channel 141 of member 150 so that catheter 110b operates as a dual lumen catheter.

It should also be noted that there are many other embodiments of catheter that can be manufactured, one of which will be discussed in more detail presently.

Figure 12A:
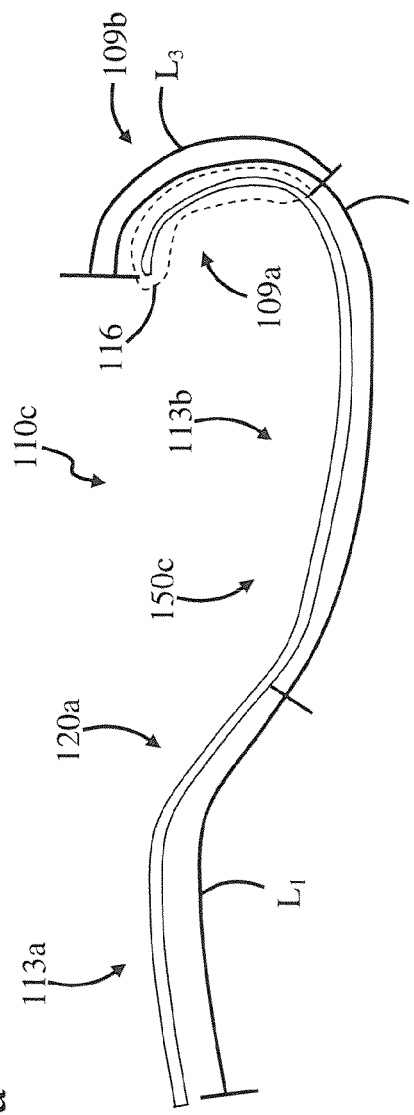
FIG. 12a is a side view of another embodiment of a catheter, which includes a non-helical reinforcement member, and a resilient tube having aspirating orifices.
Figure 12B:
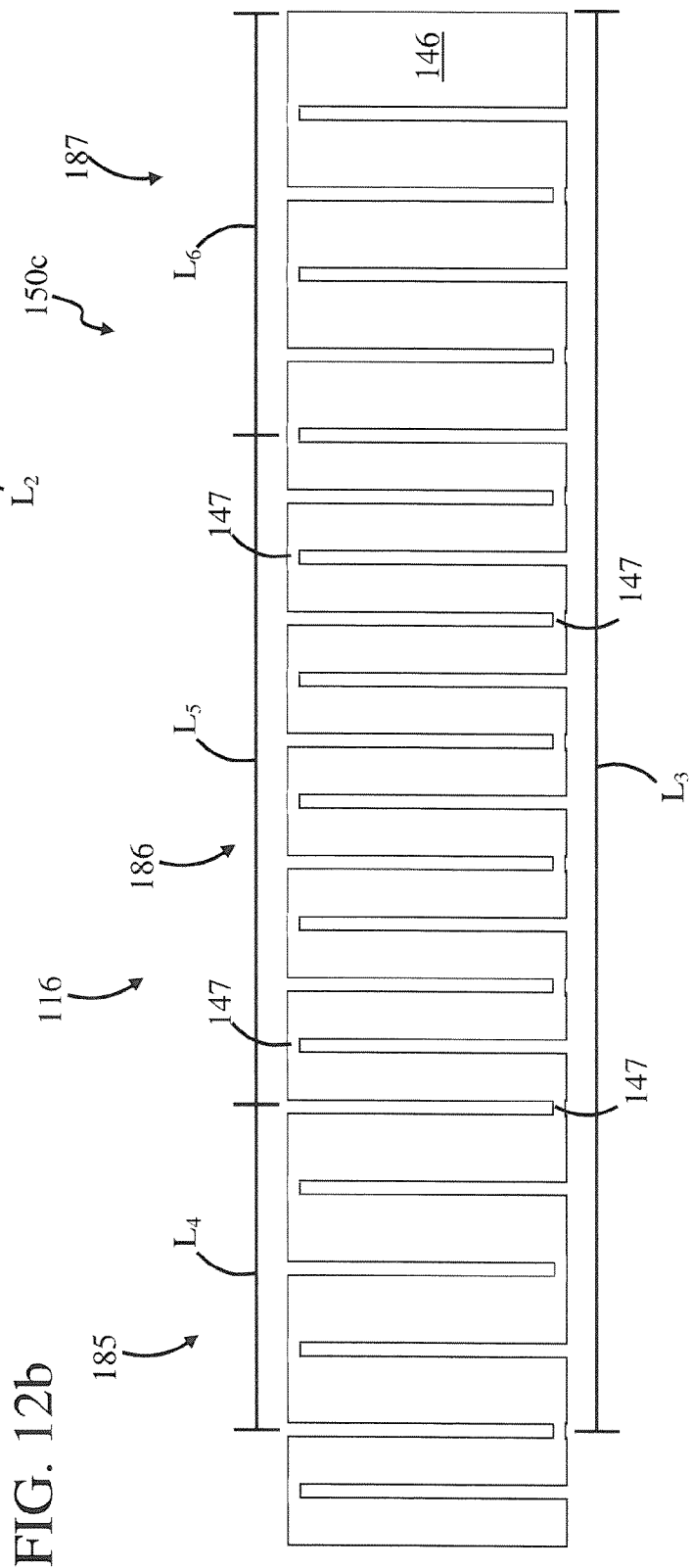
Figure 12C:
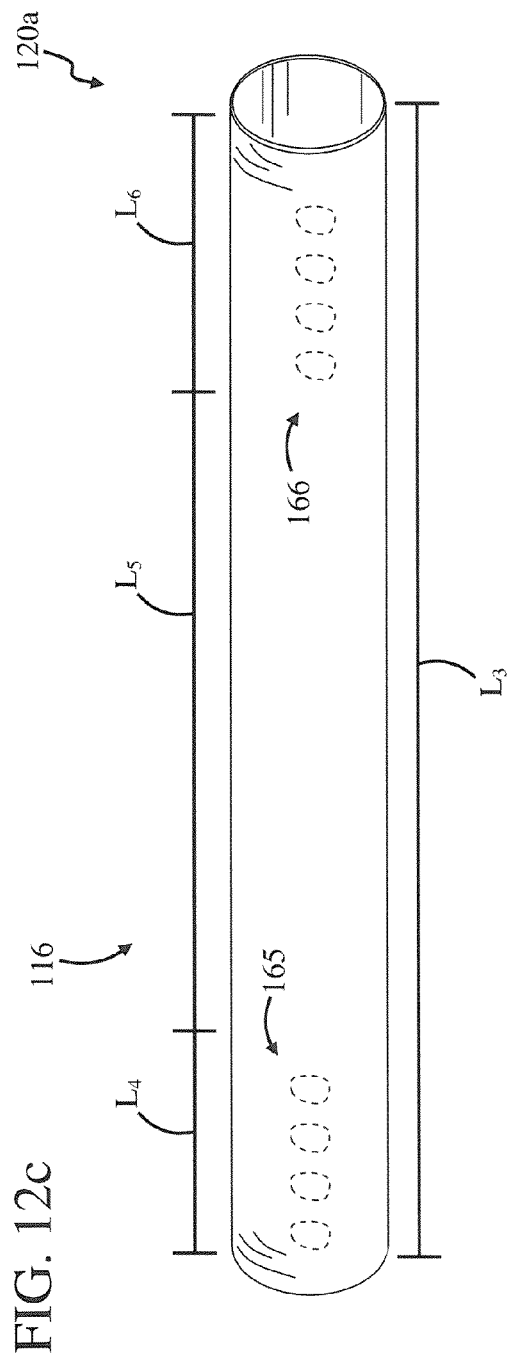
Figure 12D:
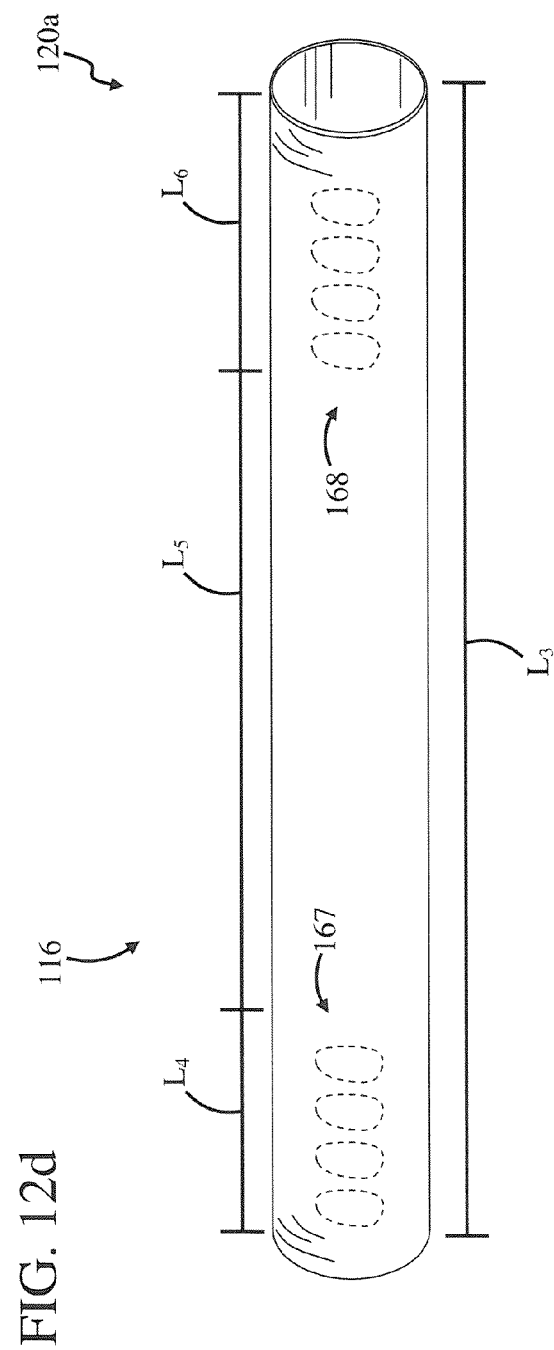

FIG. 12a is a side view of a catheter 110c, which includes a resilient tube 120a and a non-helical reinforcement member 150c. FIG. 12b is a side view of non-helical reinforcement member 150c in region 116 of FIG. 12a. FIGS. 12c and 12d are perspective views of resilient tube 120a looking in directions 109a and 109b, respectively, of FIG. 12a.

As shown in FIG. 12a, catheter 110c includes proximal portion 113a and distal portion 113b. Proximal portion 113a and distal portion 113b have lengths $L_1$ and $L_2$, respectively. Lengths $L_1$ and $L_2$ can have many different values. For example, in one embodiment, length $L_1$ is between about eight inches to about fifteen inches, and length $L_2$ is between about thirty inches to about forty inches. It is desirable for proximal portion 113a to be able to extend through nasal passage 101 and esophagus 102 without kinking, such as in region 107 (FIG. 1). Further, it is desirable for distal portion 113b to be allowed to bend, but restricted from stretching and compressing.

As shown in FIGS. 12a and 12b, region 116 has a length $L_3$, along which non-helical reinforcement member 150c extends. Non-helical reinforcement member 150c includes non-helical band coils 185, which extend along a length $L_4$ of non-helical reinforcement member 150c. Non-helical reinforcement member 150c generally includes one or more non-helical band coils 185 connected together with one or more arms. Non-helical reinforcement member 150c includes non-helical band coils 186, which extend along a length $L_5$ of non-helical reinforcement member 150c. Non-helical reinforcement member 150c generally includes one or more non-helical band coils 186 connected together with one or more arms. Non-helical reinforcement member 150c includes non-helical band coils 187, which extend along a length $L_5$ of non-helical reinforcement member 150c. Non-helical reinforcement member 150c generally includes one or more non-helical band coils 187 connected together with one or more arms. The non-helical band coils of non-helical reinforcement member 150c are connected together with arms, as discussed in more detail above with FIGS. 6a-6k.

It should also be noted that length $L_3$ is equal to the sum of lengths $L_4$, $L_5$ and $L_6$. Lengths $L_3$, $L_4$, $L_5$ and $L_6$ can have many different values. In one embodiment, length $L_3$ has a value less than about fifteen inches. In some embodiments, length $L_3$ has a value between about twelve inches and eight inches.

In one embodiment, length $L_4$ has a value less than about six inches. In some embodiments, length $L_4$ has a value between about five inches and one inch.

In one embodiment, length $L_5$ has a value less than about ten inches. In some embodiments, length $L_5$ has a value between about eight inches and three inches. It should be noted that, in some embodiments, length $L_5$ is larger than length $L_4$. It should be noted that, in some embodiments, length $L_5$ is larger than length $L_6$.

In one embodiment, length $L_6$ has a value less than about six inches. In some embodiments, length $L_6$ has a value between about five inches and one inch. It should be noted that, in some embodiments, lengths $L_4$ and $L_6$ have the same values.

In this embodiment, resilient tube 120a includes aspirating orifices 165 and 166 on the side of tube 120a looking in direction 109a, as indicated in FIG. 12a. Aspirating orifices 166 are positioned towards the distal end of resilient tube 120a and extend along length $L_6$. Aspirating orifices 165 are positioned so they extend along length $L_4$. Hence, aspirating orifices 165 and 166 are spaced from each other by about length $L_5$.

In this embodiment, resilient tube 120a includes aspirating orifices 167 and 168 on the side of tube 120b looking in direction 109b, as indicated in FIG. 12a. Aspirating orifices 167 are positioned towards the distal end of resilient tube 120b and extend along length $L_6$. Aspirating orifices 167 are positioned so they extend along length $L_4$. Hence, aspirating orifices 167 and 168 are spaced from each other by about length $L_5$.

It should be noted that the sides of tube 120b looking in directions 109a and 109b are opposed to each other. Hence, in this embodiment, aspirating orifices 165 and 167 are opposed to each other. Further, aspirating orifices 166 and 168 are opposed to each other. In this embodiment, aspirating orifices 165 and 166 are the same size, and are oval in shape. Further, in this embodiment, aspirating orifices 165 and 166 are the same size, and are oval in shape. In this embodiment, aspirating orifices 165 and 167 are larger in size than aspirating orifice 165 and 166.

Aspirating orifices 165, 166, 167 and 168 can have many different sizes. In one embodiment, the major axis of aspirating orifices 165 and 166 are between about 0.05 inches to about 0.12 inches, and the major axis is between about 0.06 inches and 0.15 inches. It should be noted that aspirating orifices 165 and 166 are circular when the major and minor axes are equal.

In one embodiment, the major axis of aspirating orifices 167 and 168 are between about 0.08 inches to about 0.25 inches, and the major axis is between about 0.09 inches and 0.30 inches. It should be noted that aspirating orifices 167 and 168 are circular when the major and minor axes are equal.

Figure 13A:
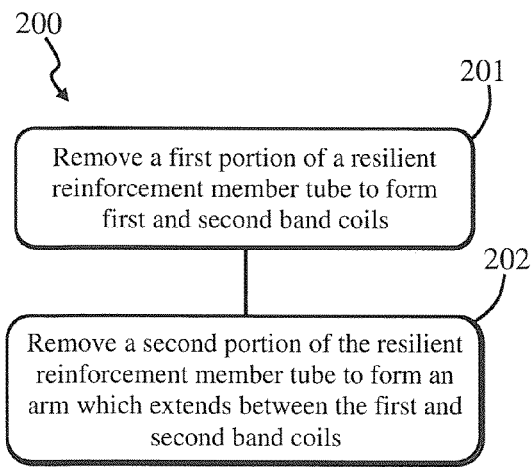
FIGS. 13a, 13b and 13c are flow diagrams of methods of manufacturing a reinforcement member.

FIG. 13a is a flow diagram of a method 200 of manufacturing a reinforcement member. In this embodiment, method 200 includes a step 201 of removing a first portion of a resilient reinforcement member tube to form first and second band coils.

In this embodiment, method 200 includes a step 202 of removing a second portion of the resilient reinforcement member tube to form an arm which extends between the first and second band coils. The arm restricts the ability of the first and second band coils to move towards and away from each other.

Figure 13B:
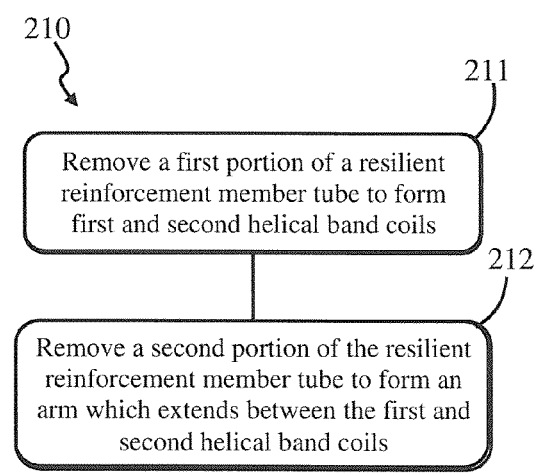

FIG. 13b is a flow diagram of a method 210 of manufacturing a helical reinforcement member. In this embodiment, method 210 includes a step 211 of removing a first portion of a resilient reinforcement member tube to form first and second helical band coils.

In this embodiment, method 210 includes a step 212 of removing a second portion of the resilient reinforcement member tube to form an arm which extends between the first and second helical band coils. The arm restricts the ability of the first and second helical band coils to move towards and away from each other.

Figure 13C:
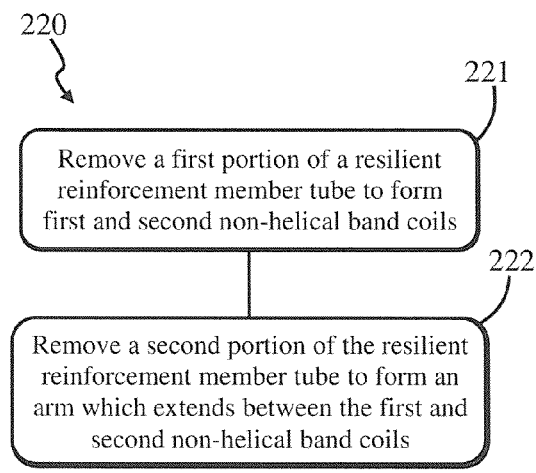

FIG. 13c is a flow diagram of a method 220 of manufacturing a non-helical reinforcement member. In this embodiment, method 220 includes a step 221 of removing a first portion of a resilient reinforcement member tube to form first and second non-helical band coils.

In this embodiment, method 220 includes a step 222 of removing a second portion of the resilient reinforcement member tube to form an arm which extends between the first and second non-helical band coils. The arm restricts the ability of the first and second non-helical band coils to move towards and away from each other.

Figure 14A:
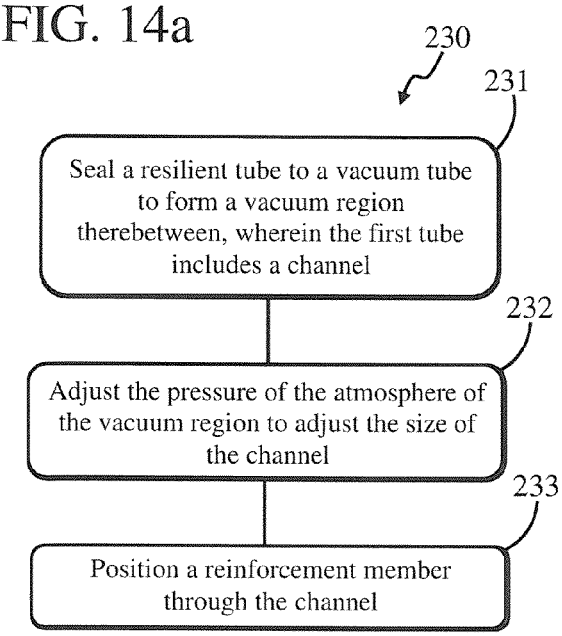
FIGS. 14a and 14b are flow diagrams of methods of manufacturing a catheter.

FIG. 14a is a flow diagram of a method 230 of manufacturing a catheter. In this embodiment, method 230 includes a step 231 of sealing a resilient tube to a vacuum tube to form a vacuum region therebetween, wherein the first tube includes a channel.

Method 230 includes a step 232 of adjusting the pressure of the atmosphere of the vacuum region to adjust the size of the channel. Step 232 can include decreasing the pressure of the atmosphere of the vacuum region to expand the channel. Step 232 can include increasing the pressure of the atmosphere of the vacuum region to contract the channel.

Method 230 includes a step 233 of positioning a reinforcement member through the channel. In some embodiments, the reinforcement member is allowed to bend and is restricted from stretching. In some embodiments, the reinforcement member includes first and second coils coupled together with an arm.

In some embodiments, method 230 includes a step of increasing the pressure of the atmosphere of the vacuum region to contract the channel so that the resilient tube is stretched around the reinforcement member.

Figure 14B:
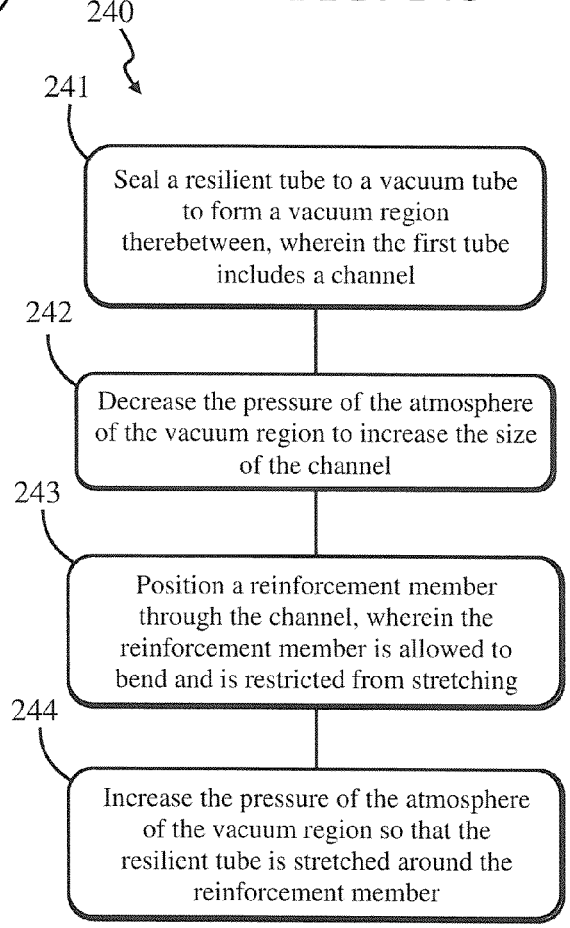

FIG. 14b is a flow diagram of a method 240 of manufacturing a catheter. In this embodiment, method 240 includes a step 241 of sealing a resilient tube to a vacuum tube to form a vacuum region therebetween, wherein the first tube includes a channel. In some embodiments, step 241 includes folding opposed ends of the resilient tube over the vacuum tube to form a seal therebetween. In some embodiments, step 241 includes clamping opposed ends of the resilient tube to the vacuum tube to form a seal therebetween.

Method 240 includes a step 242 of decreasing the pressure of the atmosphere of the vacuum region to increase the size of the channel.

Method 240 includes a step 243 of positioning a reinforcement member through the channel, wherein the reinforcement member is allowed to bend and is restricted from stretching. In some embodiments, the reinforcement member includes first and second coils coupled together with an arm. In some embodiments, the reinforcement member is a helical reinforcement member and, in other embodiments, the reinforcement member is a non-helical reinforcement member.

In this embodiment, method 240 includes a step 244 of increasing the pressure of the atmosphere of the vacuum region so that the resilient tube is stretched around the reinforcement member.

It should be noted that the steps in the methods disclosed herein can be carried out in many different orders. It should also be noted that the catheters of the methods disclosed herein generally include one or more lumens. Further, in some embodiments, the catheters can be included in a dual lumen device. For example, the catheter can be attached to and carried by an aspiration tube, wherein the aspiration tube can include inner and outer layers of resilient material with a spring positioned between them. The methods disclosed herein can include one or more of the steps disclosed in the methods described in U.S. patent application Ser. No. 11/838,657, which is incorporated by reference as though fully set forth herein.

The embodiments of the invention described herein are exemplary and numerous modifications, variations and rearrangements can be readily envisioned to achieve substantially equivalent results, all of which are intended to be embraced within the spirit and scope of the invention.

The invention claimed is:

1. A gastrointestinal catheter comprising a heat shrink tubing having a thickness of about 0.0001 inch and overlaying the catheter proximal portion and a reinforcement member having a helical spring band, wherein a cloth mesh sleeve encases the reinforcement member entire length between the heat shrink tubing and the reinforcement member having the helical spring band.

2. The catheter of claim 1, wherein the helical spring band is a double helical spring band.

3. The catheter of claim 1, wherein the helical spring band comprises stainless steel.

4. The catheter of claim 1, wherein the cloth mesh sleeve is less than about 0.002 inches thick.

5. The catheter of claim 1, wherein the cloth mesh sleeve comprises polyester, nylon and/or a mixture thereof.

* * * * *